(12) United States Patent
Varadarajan et al.

(10) Patent No.: US 12,150,714 B2
(45) Date of Patent: *Nov. 26, 2024

(54) REVERSE SHOULDER PRE-OPERATIVE PLANNING

(71) Applicant: Biomet Manufacturing, LLC, Warsaw, IN (US)

(72) Inventors: Ravikumar Varadarajan, Warsaw, IN (US); Jeffrey E. Bischoff, Warsaw, IN (US); Clinton E. Kehres, Warsaw, IN (US); Bryce A. Isch, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 699 days.

This patent is subject to a terminal disclaimer.

(21) Appl. No.: 17/371,287

(22) Filed: Jul. 9, 2021

(65) Prior Publication Data

US 2021/0330389 A1    Oct. 28, 2021

Related U.S. Application Data

(63) Continuation of application No. 16/712,606, filed on Dec. 12, 2019, now Pat. No. 11,083,525, which is a (Continued)

(51) Int. Cl.
*A61B 34/10* (2016.01)
*G16H 50/50* (2018.01)
(Continued)

(52) U.S. Cl.
CPC ............. *A61B 34/10* (2016.02); *G16H 50/50* (2018.01); *A61B 2034/101* (2016.02);
(Continued)

(58) Field of Classification Search
USPC ............................................. 382/128; 703/11
See application file for complete search history.

(56) References Cited

U.S. PATENT DOCUMENTS

| 5,880,976 A | 3/1999 | DiGioia III et al. |
| 6,205,411 B1 | 3/2001 | DiGioia, III et al. |

(Continued)

FOREIGN PATENT DOCUMENTS

| CA | 2753488 A1 | 9/2010 |
| CA | 2927549 A1 | 4/2015 |

(Continued)

OTHER PUBLICATIONS

"U.S. Appl. No. 15/644,002, Examiner Interview Summary mailed Jul. 30, 2019", 4 pgs.

(Continued)

*Primary Examiner* — Ishrat I Sherali
(74) *Attorney, Agent, or Firm* — SCHWEGMAN LUNDBERG & WOESSNER, P.A.

(57) ABSTRACT

A method of pre-operatively developing a reverse shoulder arthroplasty plan can include receiving an image of a patient shoulder comprising a humerus and a glenoid. The image can be segmented to develop a 3D shoulder model. Virtual surgery can be performed on the 3D shoulder model to generate a modified shoulder model. The virtual surgery can include resecting and reaming a virtual humerus of the 3D shoulder model, and reaming a virtual glenoid of the 3D shoulder model. Selection of a humeral implant and selection of a glenoid implant can be received. A virtual representation of the humeral implant can be implanted on the virtual humerus and a virtual representation of the glenoid implant on the virtual glenoid to virtually update the modified shoulder model. A range of motion of the patient shoulder can be determined and a reverse shoulder arthroplasty can be finalized based on the range of motion.

20 Claims, 16 Drawing Sheets

Related U.S. Application Data continuation of application No. 15/644,002, filed on Jul. 7, 2017, now Pat. No. 10,537,390.

(60) Provisional application No. 62/476,112, filed on Mar. 24, 2017, provisional application No. 62/360,140, filed on Jul. 8, 2016.

(51) Int. Cl.
*A61B 34/00* (2016.01)
*A61F 2/40* (2006.01)

(52) U.S. Cl.
CPC ... *A61B 2034/104* (2016.02); *A61B 2034/105* (2016.02); *A61B 2034/108* (2016.02); *A61B 34/25* (2016.02); *A61F 2/4014* (2013.01)

(56) References Cited

U.S. PATENT DOCUMENTS

| | | | |
|---|---|---|---|
| 8,556,983 B2 | 10/2013 | Bojarski et al. | |
| 9,439,767 B2 | 9/2016 | Bojarski et al. | |
| 9,956,047 B2* | 5/2018 | Bojarski | A61B 17/155 |
| 10,456,263 B2* | 10/2019 | Bojarski | A61B 17/157 |
| 10,537,390 B2* | 1/2020 | Varadarajan | A61B 34/10 |
| 10,987,175 B2* | 4/2021 | Britton | A61B 34/70 |
| 11,083,525 B2* | 8/2021 | Varadarajan | A61B 34/10 |
| 11,419,680 B2* | 8/2022 | Kontaxis | A61B 34/10 |
| 2003/0184577 A1 | 10/2003 | Petrella et al. | |
| 2005/0065617 A1 | 3/2005 | Moctezuma De la Barrera et al. | |
| 2008/0269906 A1 | 10/2008 | Iannotti et al. | |
| 2011/0010187 A1 | 1/2011 | Andersson et al. | |
| 2014/0107654 A1 | 4/2014 | Kehres et al. | |
| 2015/0073424 A1 | 3/2015 | Couture et al. | |
| 2016/0045317 A1* | 2/2016 | Lang | A61F 2/30942 700/98 |
| 2016/0217268 A1 | 7/2016 | Otto et al. | |
| 2016/0270854 A1 | 9/2016 | Chaoui | |
| 2016/0324581 A1 | 11/2016 | Bojarski et al. | |
| 2018/0008350 A1 | 1/2018 | Varadarajan et al. | |
| 2020/0113632 A1 | 4/2020 | Varadarajan et al. | |

FOREIGN PATENT DOCUMENTS

| | | |
|---|---|---|
| GB | 2484042 B | 3/2014 |
| WO | WO-2013062851 A1 | 5/2013 |
| WO | WO-2015052586 A2 | 4/2015 |
| WO | WO-2016180438 A1 | 11/2016 |
| WO | WO-2016180439 A1 | 11/2016 |
| WO | WO-2018009794 A1 | 1/2018 |

OTHER PUBLICATIONS

"U.S. Appl. No. 15/644,002, Non Final Office Action mailed Jan. 31, 2019", 13 pgs.
"U.S. Appl. No. 15/644,002, Non Final Office Action mailed May 6, 2019", 16 pgs.
"U.S. Appl. No. 15/644,002, Notice of Allowance mailed Sep. 13, 2019", 8 pgs.
"U.S. Appl. No. 15/644,002, Response filed Jan. 3, 2019 to Restriction Requirement mailed Oct. 9, 2018", 9 pgs.
"U.S. Appl. No. 15/644,002, Response filed Apr. 18, 2019 to Non Final Office Action mailed Jan. 31, 2019", 12 pgs.
"U.S. Appl. No. 15/644,002, Response filed Jul. 31, 2019 to Non-Final Office Action mailed May 6, 2019", 13 pgs.
"U.S. Appl. No. 15/644,002, Restriction Requirement mailed Oct. 9, 2018", 6 pgs.
"U.S. Appl. No. 16/712,606, Examiner Interview Summary mailed Jan. 13, 2021", 2 pgs.
"U.S. Appl. No. 16/712,606, Non Final Office Action mailed Dec. 24, 2020", 9 pgs.
"U.S. Appl. No. 16/712,606, Notice of Allowance mailed Apr. 7, 2021", 7 pgs.
"U.S. Appl. No. 16/712,606, Preliminary Amendment filed Dec. 16, 2019", 7 pgs.
"U.S. Appl. No. 16/712,606, Response filed Mar. 24, 2021 to Non Final Office Action mailed Dec. 24, 2020", 10 pgs.
"U.S. Appl. No. 16/712,606, Response filed Nov. 23, 2020 to Restriction Requirement mailed Sep. 22, 2020", 8 pgs.
"U.S. Appl. No. 16/712,606, Restriction Requirement mailed Sep. 22, 2020", 6 pgs.
"European Application Serial No. 17740261.7 Response to Communication pursuant to Rules 161(1) and 162 EPC filed Sep. 9, 2019", 16 pgs.
"European Application Serial No. 17740261.7, Communication Pursuant to Article 94(3) EPC mailed May 11, 2020", 4 pgs.
"European Application Serial No. 17740261.7, Response filed Nov. 23, 2020 to Communication Pursuant to Article 94(3) EPC mailed May 11, 2020", 20 pgs.
"International Application Serial No. PCT/US2017/041097, International Preliminary Report on Patentability mailed Jan. 17, 2019", 17 pgs.
"International Application Serial No. PCT/US2017/041097, International Search Report mailed Dec. 18, 2017", 8 pgs.
"International Application Serial No. PCT/US2017/041097, Invitation to Pay Add'l Fees and Partial Search Report mailed Oct. 19, 2017", 1 Pg.
"International Application Serial No. PCT/US2017/041097, Written Opinion mailed Dec. 18, 2017", 15 pgs.
3delab.com, "Hip Range of Motion Simulation", 3delab.com youtube, Retrieved from the Internet URL <https //www.youtube com/ watchvGTWAbZUR7Fc> Retrieved on Oct. 2, 2017, (Aug. 8, 2012), 1 pg.
Botha, Charl P. et al., "Pre-operative Planning and Intra-operative Guidance for Shoulder Replacement Surgery", 1998 ACM Subject Classification I.3.8 Applications, J.3 Life and Medical Sciences, (Jan. 1, 2010), 17 pgs.
Krekel, et al., "Interactive simulation and comparative visualisation of the bone-determined range of motion of the human shoulder", Simulation und Visualisierung 2006 SIMVIS 2, SCS-Verlag Magdeburg, Germany, (Jan. 1, 2006), 13 pgs.
Moctezuma, et al., "Assessment of the Hip Range of Motion Envelope in Total Hip Arthroplasty using Graphical Interface", 56th Annual Meeting of the Orthopaedic Research Society, (Mar. 9, 2010), 1 pg.
Turley, G A, "Establishing a range of motion boundary for total hip arthroplasty", Proceedings of the Institution of Mechanical Engineers. Journal of Engineering in Medicine Part H., vol. 225 No. 8, (Aug. 1, 2011), 1-14.
Widmer, K H, "Containment versus impingement finding compromise for cup placement in total hip arthroplasty", International Orthopaedics Springer Berlin DE vol. 31 No. 1, (Jul. 28, 2007), 11 pgs.
Widmer, K. H, et al., "Compliant positioning of total hip components for optimal range of motion", Journal of Orthopaedic Research vol. 22 No. 4, (Jul. 1, 2004), 815-821.
Zhou, Hai, et al., "Motion performance and impingement risk of total hip arthroplasty with simulation module", Zhejiang University Journal Science B: International Biomedicine Biotechnology Journal vol. 14 No. 9, (Sep. 1, 2013), 10 pgs.
U.S. Appl. No. 15/644,002 U.S. Pat No. 10,537,390, filed Jul. 7, 2017, Reverse Shoulder Pre-Operative Planning.
U.S. Appl. No. 16/712,606, filed Dec. 12, 2019, Reverse Shoulder Pre-Operative Planning.

\* cited by examiner

REVERSE SHOULDER PRE-OPERATIVE PLANNING

CLAIM OF PRIORITY

This application is a continuation of U.S. patent application Ser. No. 16/712,606, filed on Dec. 12, 2019, which is a continuation of U.S. patent application Ser. No. 15/644,002, filed on Jul. 7, 2017, which claims the benefit of U.S. Provisional Patent Application Ser. No. 62/360,140, filed on Jul. 8, 2016, and U.S. Provisional Patent Application Ser. No. 62/476,112, filed on Mar. 24, 2017, the benefit of priority of each are claimed hereby, and which are incorporated by reference herein in its entirety.

FIELD

The present subject matter relates to orthopedic procedures and, more particularly, to systems and methods that can aid in performing reverse shoulder arthroplasties.

BACKGROUND

The shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

The shoulder joint can undergo degenerative changes caused by various issues, such as rheumatoid arthritis, osteoarthritis, rotator cuff arthroplasty, vascular necrosis, or bone fracture. When severe joint damage occurs and no other means of treatment is found to be effective, a total, partial, or reverse shoulder replacement or reconstruction may be necessary. Reverse shoulder replacements can include a cup shaped articular surface attached to a stem implanted into the humerus, while a spherical glenoid component is used to provide an articular surface to engage the humeral cup.

OVERVIEW

During shoulder arthroplasty surgery, the components of the prosthesis are matched with the biology of the patient in an effort to maintain or restore a natural range of motion of a healthy shoulder joint. Patient specific instrumentation can assist a surgeon in planning and implementing a shoulder arthroplasty to restore natural movement. However, even with the multitude of advances in prosthetic components and patient specific instrumentation, restoring a full range of motion can remain difficult, especially for a surgeon who does not regularly perform shoulder replacements. In some cases, range of motion of a patient following a successful procedure is limited more than is desirable to some patients.

The systems, devices, methods, and instruments discussed herein can provide virtual calculations and measurements to assist surgeons in determining whether virtual prosthetic devices may provide a patient with desirable outcomes. By determining range of motion, conditions of operation, and probability of joint functions, a pre-operative plan can be developed to provide standards of care that more routinely result in successful outcomes. Well-formed pre-operative plans can also result in more successful outcomes over intra-operative selection of prostheses and installation provisions, such as resection and reaming.

While the above discusses issues and procedures specific to shoulder replacement procedures, discussion of the following systems, devices, methods, and instruments is also applicable for use in other joint replacement procedures, such as anatomic total shoulder arthroplasty (aTSA), total hip arthroplasty (THA) or total knee arthroplasty (TKA). Further, the systems, devices, methods, and instruments may also be applicable to aspects of partial knee replacements and other orthopedic procedures to repair of joints.

To further illustrate the apparatuses and systems disclosed herein, the following non-limiting examples are provided:

Example 1 is a method of pre-operatively developing a reverse shoulder arthroplasty plan, the method can include: receiving an image of a patient shoulder comprising a humerus and a glenoid; segmenting the image to develop a 3D shoulder model; performing virtual surgery on the 3D shoulder model to generate a modified shoulder model, the virtual surgery comprising: resecting and reaming a virtual humerus of the 3D shoulder model; reaming a virtual glenoid of the 3D shoulder model; receiving selection of a humeral implant; receiving selection of a glenoid implant; implanting, virtually to update the modified shoulder model, a virtual representation of the humeral implant on the virtual humerus and a virtual representation of the glenoid implant on the virtual glenoid; determining a range of motion of the patient shoulder based on analysis of the updated modified shoulder model including determining an expected interaction between the virtual representation of the humerus implant and the virtual representation of the glenoid implant after the selected virtual humeral implant and the selected virtual glenoid implant are virtually implanted; and finalizing a reverse shoulder arthroplasty plan when the range of motion is within a desired range and receiving selection of at least one of a second humeral implant and a second glenoid implant when the range of motion is not within the desired range.

In Example 2, the subject matter of Example 1 optionally includes displaying on a user interface a graphic representation of the range of motion.

In Example 3, the subject matter of Example 2 optionally includes displaying on the graphic representation of the range of motion and a range of motion required to perform a common daily activity.

In Example 4, the subject matter of any one or more of Examples 2-3 optionally include determining whether the updated modified shoulder model can perform the common daily activity as a function of the range of motion.

In Example 5, the subject matter of any one or more of Examples 2-4 optionally include displaying on the graphic representation of the range of motion and a range of motion required to perform a second common daily activity; and determining whether the updated modified shoulder model can perform the second common daily activity as a function of the range of motion.

In Example 6, the subject matter of any one or more of Examples 2-5 optionally include identifying collisions between components of the updated modified shoulder model; and developing the range of motion as a function of the identified collisions.

In Example 7, the subject matter of Example 6 optionally includes identifying areas of collision as a function of the identified collisions; and displaying on the graphic representation of the range of motion, the identified areas of collision.

In Example 8, the subject matter of any one or more of Examples 1-7 optionally include wherein: the virtual representation of the humeral implant includes a humeral implant thickness, offset, articulation surface radius, implant version, and position on the virtual humerus; and the virtual representation of the glenoid implant includes a glenoid implant thickness, offset, eccentricity, and position on the virtual glenoid.

In Example 9, the subject matter of Example 8 optionally includes wherein receiving selection of the humeral implant includes selecting the humeral implant from a library of humeral implants as a function of the humeral implant thickness, offset, articulation surface radius, implant version, and position on the virtual humerus; and wherein receiving selection of the glenoid implant includes selecting the glenoid implant from a library of glenoid implants as a function of the glenoid implant thickness, offset, eccentricity, and position on the virtual glenoid.

In Example 10, the subject matter of Example 9 optionally includes receiving a thickness adjustment of at least one of the humeral implant and the glenoid implant when the range of motion is not within the desired range; receiving an offset adjustment of at least one of the humeral implant relative to the humerus and the glenoid implant relative to the glenoid when the range of motion is not within the desired range; and receiving a position adjustment of at least one of the humeral implant on the virtual humerus and the glenoid implant on the virtual glenoid when the range of motion is not within the desired range.

In Example 11, the subject matter of any one or more of Examples 9-10 optionally include selecting a base virtual representation of the humeral implant and a base virtual representation of the glenoid implant as a function of adjusting at least one of thickness, offset, and position of the virtual representation of the humeral implant and the virtual representation of the glenoid implant.

In Example 12, the subject matter of Example 11 optionally includes displaying a graphic representation on a user interface of a range of motion of the updated modified shoulder model including the base virtual representation of the humeral implant and the base virtual representation of the glenoid implant; and adjusting at least one of the base virtual representation of the humeral implant and the base virtual representation of the glenoid implant using the user interface.

In Example 13, the subject matter of any one or more of Examples 11-12 optionally include adjusting the virtual surgery as a function of at least one of the base virtual humeral implant and a base virtual glenoid implant.

In Example 14, the subject matter of any one or more of Examples 1-13 optionally include determining a probability of one or more of joint loosening, dislocation, laxity, and muscle activation; and adjusting at least one of the base virtual representation of the humeral implant and the base virtual representation of the glenoid implant as a function of the probability of one or more of joint loosening, dislocation, laxity, and muscle activation.

Example 15 is a method of pre-operatively developing a shoulder arthroplasty plan, the method comprising: receiving an image of a patient shoulder comprising a humerus and a glenoid; segmenting the image to develop a 3D shoulder model; selecting, based at least in part on the 3D shoulder model; a humeral implant; selecting, base at least in part on the 3D shoulder model, a glenoid implant; positioning within the 3D shoulder model a virtual representation of the humeral implant on the virtual humerus and a virtual representation of the glenoid implant on the virtual glenoid; analyzing the 3D shoulder model with the virtual representation of the humeral implant and the virtual representation of the glenoid to determine a condition of the patient shoulder including determining an expected interaction between the humerus implant and the glenoid implant; and generating a shoulder arthroplasty plan based at least in part on the condition.

In Example 16, the subject matter of Example 15 optionally includes wherein the condition is a range of motion of the patient shoulder.

In Example 17, the subject matter of any one or more of Examples 15-16 optionally include wherein the analysis includes finite element analysis.

In Example 18, the subject matter of Example 17 optionally includes wherein in the condition includes one or more of a humeral force, a humeral stress, a humeral strain, a glenoid force, a glenoid stress, a glenoid strain, a humeral implant force, a humeral implant stress, a humeral implant strain, a glenoid implant force, a glenoid implant stress, a glenoid implant strain, a soft tissue force, a soft tissue stress, and a soft tissue strain.

In Example 19, the subject matter of Example 18 optionally includes displaying a graphic representation on a user interface of the condition of the updated modified shoulder model including the virtual representation of the humeral implant and the virtual representation of the glenoid implant; and adjusting at least one of the base virtual representation of the humeral implant and the base virtual representation of the glenoid implant using the user interface.

In Example 20, the subject matter of any one or more of Examples 17-19 optionally include wherein: the virtual representation of the humeral implant includes a humeral implant thickness, offset, and position on the virtual humerus; the virtual representation of the glenoid implant includes a glenoid implant thickness, offset, and position on the virtual glenoid; and the selection of one or more of the humeral implant and the glenoid implant can be updated by updating a selection of one or more of the thickness, offset, and position of the virtual representation of the humeral implant and virtual representation of the glenoid implant.

In Example 21, the subject matter of any one or more of Examples 17-20 optionally include aborting an iteration of the finite element analysis of the updated modified shoulder model when one of a maximum humeral force, a maximum humeral stress, a maximum humeral strain, a glenoid maximum force, a glenoid maximum stress, a glenoid maximum strain, a soft tissue maximum force, and a soft tissue force minimum force can be determined during the finite element analysis.

In Example 22, the subject matter of any one or more of Examples 17-21 optionally include wherein the finite element analysis of the updated modified shoulder model can be performed on a static model of the updated modified shoulder model.

In Example 23, the subject matter of any one or more of Examples 17-22 optionally include wherein the finite element analysis of the updated modified shoulder model can be performed on a dynamic model of the updated modified shoulder including finite element analysis of the updated modified shoulder model throughout a range of motion of the updated modified shoulder model.

Example 24 is a method of pre-operatively developing a reverse shoulder arthroplasty plan, the method comprising: receiving an image of a patient shoulder comprising a humerus and a glenoid; segmenting the image to develop a 3D shoulder model; performing virtual surgery on the 3D shoulder model to generate a modified shoulder model, the virtual surgery comprising: resecting and reaming a virtual humerus of the 3D shoulder model; reaming a virtual glenoid of the 3D shoulder model; receiving selection of a humeral implant; receiving selection of a glenoid implant; implanting, virtually to update the modified shoulder model, a virtual representation of the humeral implant on the virtual humerus and a virtual representation of the glenoid implant on the virtual glenoid; determining a range of motion of the patient shoulder based on analysis of the updated modified shoulder model including determining an expected interaction between the virtual representation of the humerus implant and the virtual representation of the glenoid implant after the selected virtual humeral implant and the selected virtual glenoid implant are virtually implanted; and finalizing a reverse shoulder arthroplasty plan when the range of motion is within a desired range and receiving selection of at least one of a second humeral implant and a second glenoid implant when the range of motion is not within the desired range.

In Example 25, the subject matter of Example 24 optionally includes displaying on a user interface a graphic representation of the range of motion.

In Example 26, the subject matter of any one or more of Examples 24-25 optionally include displaying on the graphic representation of the range of motion and a range of motion required to perform a common daily activity.

In Example 27, the subject matter of any one or more of Examples 24-26 optionally include determining whether the updated modified shoulder model can perform the common daily activity as a function of the range of motion.

In Example 28, the subject matter of any one or more of Examples 24-27 optionally include displaying on the graphic representation of the range of motion and a range of motion required to perform a second common daily activity; and determining whether the updated modified shoulder model can perform the second common daily activity as a function of the range of motion.

In Example 29, the subject matter of any one or more of Examples 24-28 optionally include identifying collisions between components of the updated modified shoulder model; and developing the range of motion as a function of the identified collisions.

In Example 30, the subject matter of any one or more of Examples 24-29 optionally include identifying areas of collision as a function of the identified collisions; and displaying on the graphic representation of the range of motion, the identified areas of collision.

In Example 31, the subject matter of any one or more of Examples 24-30 optionally include wherein: the virtual representation of the humeral implant includes a humeral implant thickness, offset, articulation surface radius, implant version, and position on the virtual humerus; and the virtual representation of the glenoid implant includes a glenoid implant thickness, offset, eccentricity, and position on the virtual glenoid.

In Example 32, the subject matter of any one or more of Examples 24-31 optionally include wherein receiving selection of the humeral implant includes selecting the humeral implant from a library of humeral implants as a function of the humeral implant thickness, offset, articulation surface radius, implant version, and position on the virtual humerus; and wherein receiving selection of the glenoid implant includes selecting the glenoid implant from a library of glenoid implants as a function of the glenoid implant thickness, offset, eccentricity, and position on the virtual glenoid.

In Example 33, the subject matter of any one or more of Examples 24-32 optionally include receiving a thickness adjustment of at least one of the humeral implant and the glenoid implant when the range of motion is not within the desired range; receiving an offset adjustment of at least one of the humeral implant relative to the humerus and the glenoid implant relative to the glenoid when the range of motion is not within the desired range; and receiving a position adjustment of at least one of the humeral implant on the virtual humerus and the glenoid implant on the virtual glenoid when the range of motion is not within the desired range.

In Example 34, the subject matter of any one or more of Examples 24-33 optionally include selecting a base virtual representation of the humeral implant and a base virtual representation of the glenoid implant as a function of adjusting at least one of thickness, offset, and position of the virtual representation of the humeral implant and the virtual representation of the glenoid implant.

In Example 35, the subject matter of any one or more of Examples 24-34 optionally include displaying a graphic representation on a user interface of a range of motion of the updated modified shoulder model including the base virtual representation of the humeral implant and the base virtual representation of the glenoid implant; and adjusting at least one of the base virtual representation of the humeral implant and the base virtual representation of the glenoid implant using the user interface.

In Example 36, the subject matter of any one or more of Examples 24-35 optionally include adjusting the virtual surgery as a function of at least one of the base virtual humeral implant and a base virtual glenoid implant.

In Example 37, the subject matter of any one or more of Examples 24-36 optionally include determining a probability of one or more of joint loosening, dislocation, laxity, and muscle activation; and adjusting at least one of the base virtual representation of the humeral implant and the base virtual representation of the glenoid implant as a function of the probability of one or more of joint loosening, dislocation, laxity, and muscle activation.

In Example 38, the subject matter of any one or more of Examples 24-37 optionally include aborting an iteration of the finite element analysis of the updated modified shoulder model when one of a maximum humeral force, a maximum humeral stress, a maximum humeral strain, a glenoid maximum force, a glenoid maximum stress, a glenoid maximum strain, a soft tissue maximum force, and a soft tissue force minimum force can be determined during the finite element analysis; and wherein the analysis includes finite element analysis, and wherein in the condition includes one or more of a humeral force, a humeral stress, a humeral strain, a glenoid force, a glenoid stress, a glenoid strain, a humeral implant force, a humeral implant stress, a humeral implant strain, a glenoid implant force, a glenoid implant stress, a glenoid implant strain, a soft tissue force, a soft tissue stress, and a soft tissue strain.

In Example 39, the system, assembly, or method of any one of or any combination of Examples 1-38 is optionally configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for shoulder replacement procedures, such as a reverse shoulder arthroplasty. In some examples, a virtual surgery can be performed and virtual representations of implant components can be selected and installed on a virtual model of a patient's humerus and glenoid. In these examples, a range of motion and/or probable joint operation can be determined and a surgical plan can be developed as a result.

Figure 1:
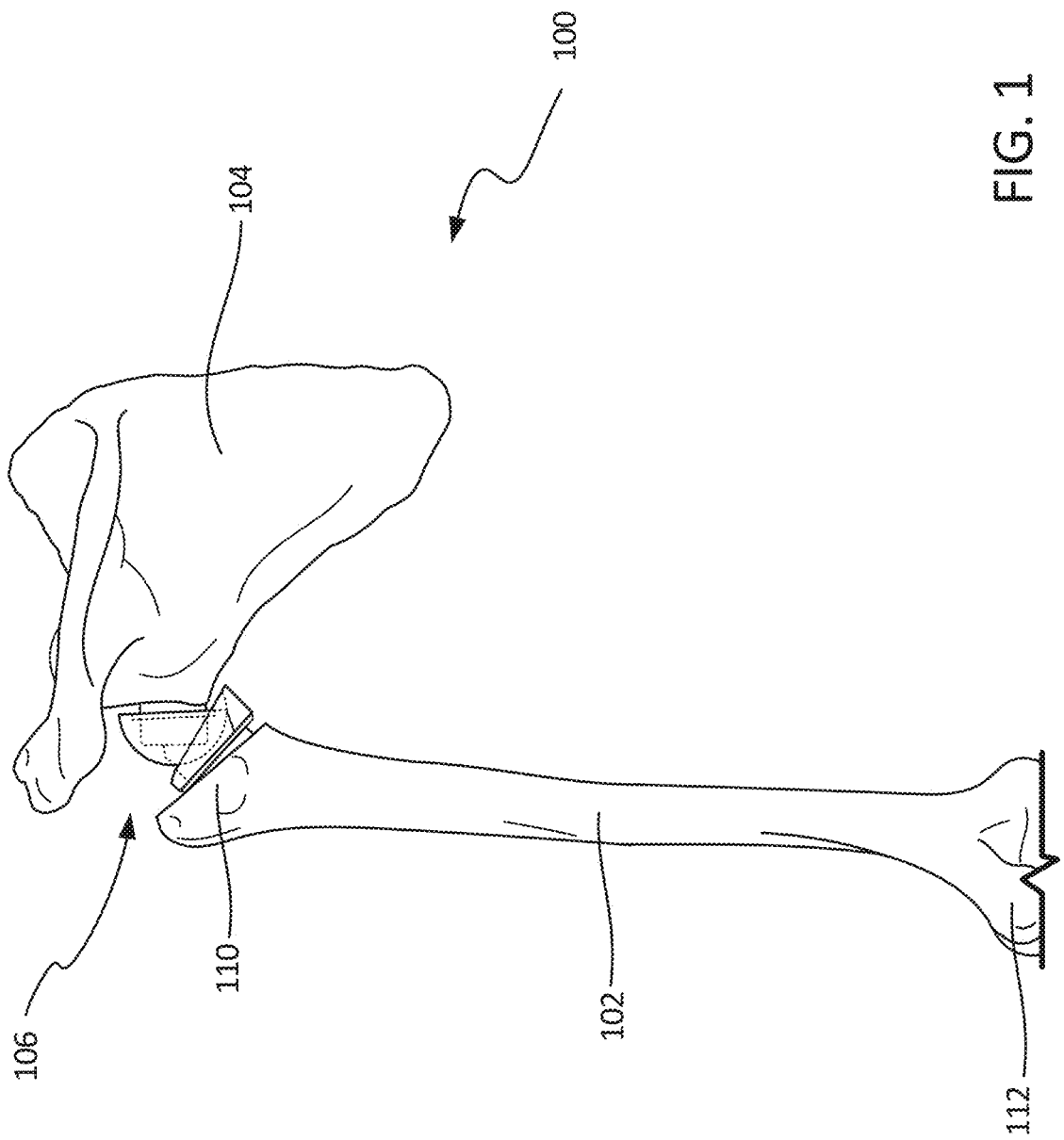
FIG. 1 illustrates an isometric view of a model of a humerus and scapula of a patient, in accordance with at least one example of this disclosure.

FIG. 1 illustrates an isometric view of model 100, which can include humerus 102, scapula 104, and implant assembly 106. Humerus 102 can include proximal resected portion 110 and distal portion 112.

Model 100 can be a modified model, where the initial model includes modeled bones created from pre-op images that would not be modified (but would include representations of the patient's pre-op anatomy, including any defects). Accordingly, model 100 can be developed from the initial model.

Humerus 102 and scapula 104 can be 3D or virtual models of a patient's humerus and scapula developed from medical images taken pre-operatively. Humerus 102 and scapula 104 can be created based on one or more images of a patient's humerus and scapula. The images can be derived from a computerized tomography (CT) scan, magnetic resonance imaging (MRI), x-ray scan, and the like. The images can be uploaded by a physician (or another person) to a system, as described further below. Once the images are uploaded they can be segmented and tuned to develop the 3D or virtual model, such as model 100 of FIG. 1.

Humerus 102 can include resected proximal portion 110, which can be configured to receive an implant, and can include distal portion 112. Resected proximal portion 110 can be derived from a virtual surgery, as discussed below, where a model of a patient's humerus, such as humerus 102, can be modified to include a resection. Implant assembly 106 can be comprised of a humeral and a glenoid component, as discussed below, where the humeral implant is implantable into the humerus and the glenoid implant is implantable into the glenoid of scapula 104.

In operation of some examples, the system can receive the images to create a virtual 3D model, as described above. Once model 100 is created, the system can perform a virtual surgery on humerus 102 and scapula 104 to generate a modified model, such as model 100 shown in FIG. 1. Thereafter, implant assembly 106 can be virtually installed on model 100 to create an updated modified model, as shown in FIG. 1. Once implant assembly 106 is installed on model 100, the system can be used to determine whether the updated modified model has a range of motion that is within a desired range. If the updated modified model has an acceptable range of motion or is deemed otherwise acceptable, a reverse shoulder arthroplasty plan can be finalized by the system. Developing a pre-operative plan for an implant assembly that provides a desired range of motion can improve the patient's quality of life and can increase procedural efficiency. As described below, this analysis can be performed in several ways.

Figure 2:
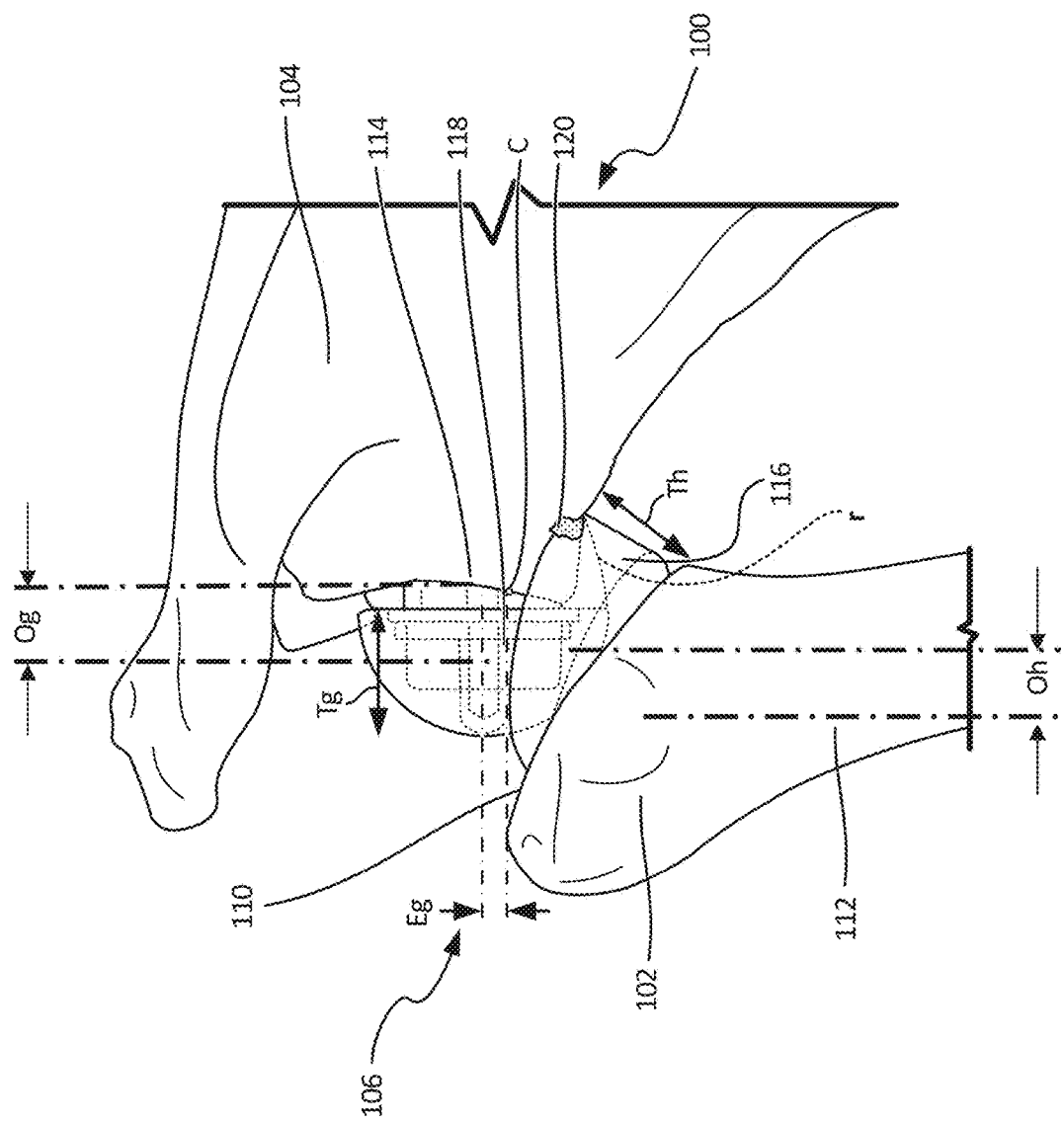
FIG. 2 illustrates a focused view of a model of a humerus and scapula of a patient, in accordance with at least one example of this disclosure.

FIG. 2 illustrates a focused view of a model 100 which can include humerus 102, scapula 104, and implant assembly 106. Humerus 102 can include proximal resected portion 110. Scapula 104 can include glenoid 114. Implant assembly 106 can include humeral implant 116 and glenoid implant 118. Also shown in FIG. 2 are humeral implant offset Oh, glenoid implant offset Og, center of rotation of glenoid sphere C, glenoid implant eccentricity Eg, humeral implant articulation radius r, humeral implant thickness Th, and glenoid thickness Tg.

Glenoid 114 of scapula 104 can be reamed and otherwise prepared to receive glenoid implant 118. Also, humerus 102 can be resected, reamed, and otherwise prepared to receive humeral implant 116.

Glenoid implant 118 and humeral implant 116 can comprise a reverse shoulder prosthetic assembly for use in a reverse shoulder arthroplasty (configured to be installed in glenoid 114 and resected proximal portion 112 of humerus 102). Humeral implant 116 can include a cup having a generally concave articulating surface configured to interface with glenoid implant 118. Glenoid implant can include a generally convex articulating surface configured to interface with humeral implant 116.

More specifically, humeral implant 116 can be a body comprised of materials such as plastics (e.g., polyethylene), and/or metal alloys (e.g. titanium alloys, stainless alloys, chromium/cobalt alloys, and the like) and combinations thereof. Glenoid implant 118 can be a body comprised of similar materials, such as plastics and/or metal alloys and combinations thereof.

Glenoid implant 118 can have a generally smooth convex geometry laterally facing humerus implant 116. Glenoid implant 118 can have a medial portion coupleable or securable to glenoid 114, such as a stem or other component inserted into a bored or reamed portion of glenoid 114. Glenoid implant 118 can include thickness Tg, which can be a material thickness partially dictating a distance that glenoid implant 118 extends in all directions from glenoid 114. Glenoid implant 118 can also have glenoid offset Og, which can be a distance that a center, in some examples, of glenoid implant 118 is offset from glenoid 114. Glenoid implant 118 can further include center C, which can be a center of rotation of the glenoid sphere about the inserted stem. When center C is offset from a centerline of the glenosphere, it can create a glenoid eccentricity Eg. FIG. 2 indicates an inferior glenoid eccentricity, however, glenoid implant 118 can be designed to include glenoid eccentricity in any direction. Both center C and glenoid eccentricity Eg can be varied to accommodate a range of motion, as desired and patient anatomy, as can be required.

Humerus implant 116 can have a generally smooth concave geometry defined by articulation surface radius r and medially facing glenoid implant 114. Articulation surface radius r can be adjustable to accommodate variations in range of motion, as required. Humerus implant 116 can have a distal portion coupleable or securable to humerus 102, such as a stem or other component inserted into a bored or reamed portion of resected proximal portion 112 of humerus 102 and can be inserted at an implant version to determine rotation of humerus implant 16 relative to a neutral axis of humerus 112 as indicated by the left axis of Oh. Humerus implant 116 can include thickness Th, which can be a material thickness partially dictating a distance that humerus implant 116 extends in all directions from humerus 102. Humerus implant 116 can also have humerus offset Oh, which can be a distance that a center, in some examples, of humerus implant 116 is offset from a neutral axis of humerus 102.

Also shown in FIG. 2 is contact point 120 (between scapular 104 and humeral implant 116). Contact point 120 can be used in at least a portion of the calculations to determine a range of motion, as described further below.

Figure 3:
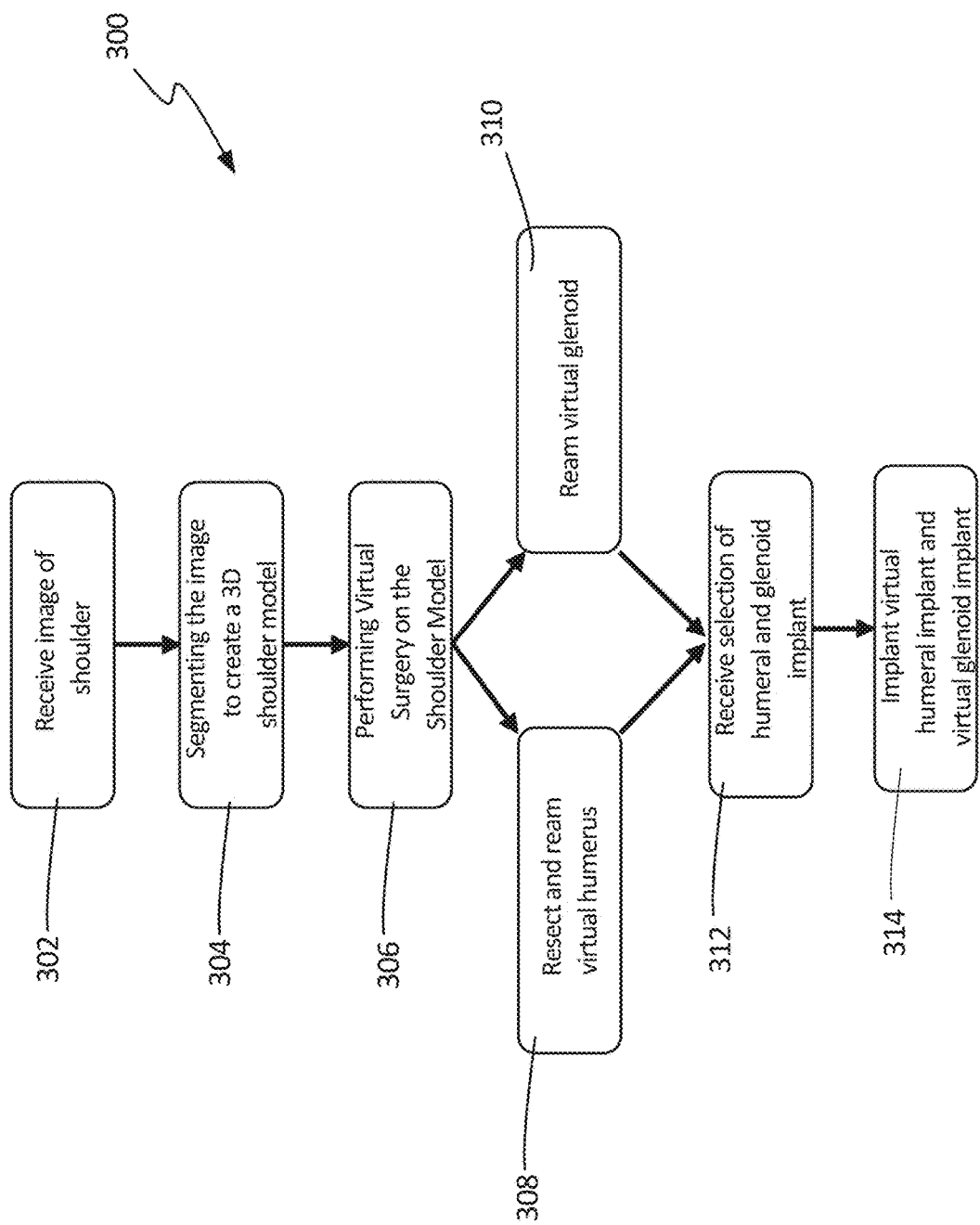
FIG. 3 illustrates a schematic view of a method of using the systems of the present disclosure, in accordance with at least one example of this disclosure.

FIG. 3 illustrates a schematic view method 300 using the devices and systems described herein, in accordance with at least one example of this disclosure. The steps or operations of method 300 (and of each method discussed herein) are illustrated in a particular order for convenience and clarity; many of the discussed operations can be performed in a different sequence or in parallel without materially impacting other operations. Method 300 as discussed includes operations performed by multiple different actors, devices, and/or systems. It is understood that subsets of the operations discussed in method 300 attributable to a single actor, device, or system could be considered a separate standalone process or method.

At step 302, method 300 can begin with receiving images of a patient's shoulder, such as from a CT or MRI, for example, as described above. Then, at step 304, the image or images can be segmented to create a 3D virtual model of the patient's shoulder. Once the model is developed, virtual surgery can be performed at step 306. The virtual surgery can include, for example, resections of bone, such as from the humerus at step 308. The virtual surgery can also include reaming of the virtual humerus at step 308 and reaming of the virtual glenoid of the scapula and at step 310. Other preparations to the bones may also be made at steps 306, 308, and 310. The virtual surgery can be performed on the 3D virtual model of the bones of the joint, in this case the shoulder, within a user interface generated by a computing system for display to a surgeon or physician. The user interface can allow the surgeon to indicate desired implant positions, resections, and/or reaming through inputs received within the 3D interface. For example, the surgeon may be able to place a resection line or plane relative to a bone or indicate an area of a bone to ream. Alternatively, resections and reaming plans may be based entirely on virtual implant positioning within the 3D interface and can be determined, at least initially, by a system considering prospective implants as well as data or equations used to determine resection locations and reaming angles. In examples, where revisions to the bones are based on implant positioning, the revisions may be determined at a later operation in method 300.

Thereafter, at step 312, selection of humeral and glenoid components can be received. The selections can either be received by the system from another system, received by the system through a user interface, or determined by the system. At step 314, the virtual humeral implant and virtual glenoid implant can be installed onto the virtual humerus and virtual glenoid, respectively. The computing system performing or enabling method 300 can generate a user interface to enable the surgeon to select and position the virtual implants in reference to the virtual bones. Method 300 can be continued at method 400, described in FIG. 4 below.

Figure 4:
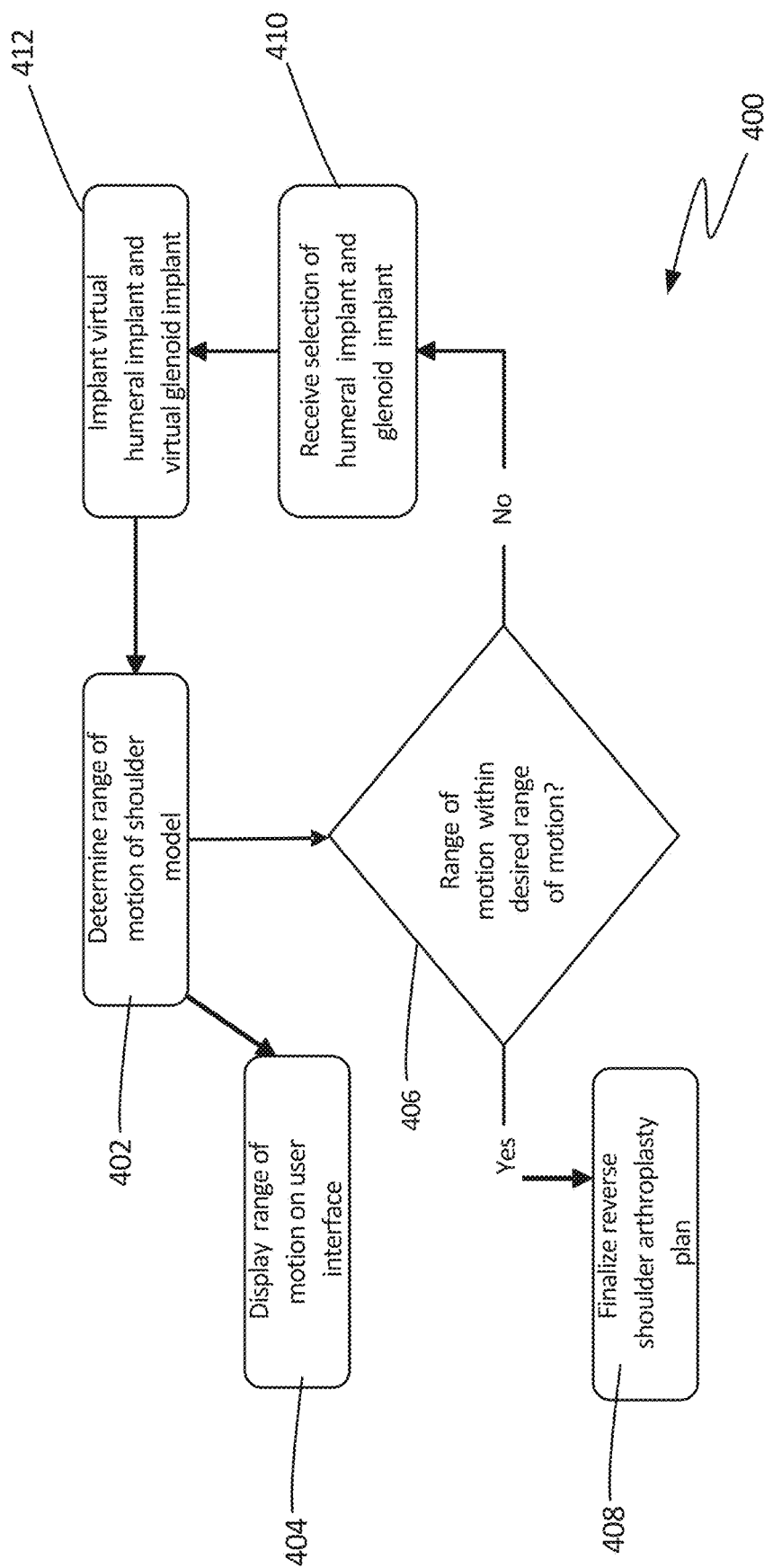
FIG. 4 illustrates a schematic view of another method of using the systems of the present disclosure, in accordance with at least one example of this disclosure.

FIG. 4 illustrates a schematic view of method 400, which can be continued from step 314 of method 300 at step 402, where a range of motion of the updated modified shoulder model can be determined using the 3D model. The range of motion can be determined from an expected interaction between the virtual humerus and the virtual glenoid after the implants have been installed. The expected interaction can be modeled using several techniques, some of which are discussed further below. In some examples, the virtual humerus (including the humeral implant) can be articulated relative to the glenoid (including the glenoid implant), where rotation is constrained by articulation of the humeral implant on the glenoid implant. As the humerus is moved through a virtual range of motion it can be noted where impact or a collision occurs between the components of the model, such as between the humeral implant and the scapula. The collisions can be charted or mapped to determine limitations of rotation of the humerus relative to the scapula.

In some other examples, the range of motion can be determined based on fit analysis. For example, data such as the thickness, offset, and placement of each insert can be compared to data from previous models and/or patients to determine an anticipated range of motion.

At step 404, the range of motion can be displayed on a user interface, such as a monitor or display. In some examples, the range of motion can be displayed as a graphical display, such as a graphic representation of a human shoulder. In other examples, a graph or chart can be used to display boundaries of the range of motion. In some other examples, the range of motion can be displayed as a list or table of limits.

At step 406, it can be determined whether the range of motion derived in step 402 is of an acceptable range of motion. This decision can be determined by a remote system, the system itself, or by a user. In some examples, the user can utilize the user interface to view the range of motion delivered at step 404 to determine whether the range of motion is within the desired range of motion. The user can then enter the decision into a system at step 406. In some other examples, the system can compare the range of motion to a typical range of motion of an average healthy, shoulder. In some other examples, the system can compare the range of motion to one or more ranges of motion required to perform daily activities, as discussed further below. In still other examples, the system can compare specific aspects of the calculated range of motion to pre-defined minimally acceptable ranges or thresholds. For example, shoulder abduction range needs to minimally reach X, and shoulder adduction range needs to minimally reach Y.

When it is determined that the range of motion is within the desired range of motion, a shoulder arthroplasty plan can be finalized at step 408. In some examples, this plan can include a written and/or pictoral plan indicating how the humerus and glenoid should be prepared. The plan can also include a detailed description of the humeral and glenoid implant. Further, the plan can include where the implants should be positioned relative to the bones and to each other. The plan may also include other information, such as incision locations, details on disconnection and reattachment of soft tissues, and the like.

When it is determined that the range of motion is not within the desired range of motion, a second humeral implant and/or second glenoid implant can be selected at step 410. As discussed in later examples, the can also be an option to reposition the selected implants and/or modify the virtual surgery. In some examples, the humeral implant and/or the glenoid implant can be selected from a library of glenoid implants and a library of humeral implants. In some examples, the library of components can be stored in a remote device, such as central device 508 of FIG. 5 (discussed below).

The second humeral implant and the second glenoid implant can be installed on the virtual humerus and virtual glenoid, respectively, at step 412, so that a second range of motion can be determined at step 402 and so that it can be determined if the second range of motion is within the desired range of motion at step 406. In some examples, following one or more iteration of the steps of method 400, the virtual surgery can be modified. That is, at least steps 406, 408, and 410 of method 400 can be performed in an attempt to obtain a desirable range of motion. In some examples, the virtual surgery can be modified and the implants may not be reselected and in some examples the virtual surgery can be modified and the implants can be re-selected. Steps 402, 406, 410, and 412 can be repeated as necessary until an acceptable range of motion is determined, at which point step 408 can be performed.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), memory cards or sticks, random access memories (RAMs), read only memories (ROMs), and the like.

Figure 5:
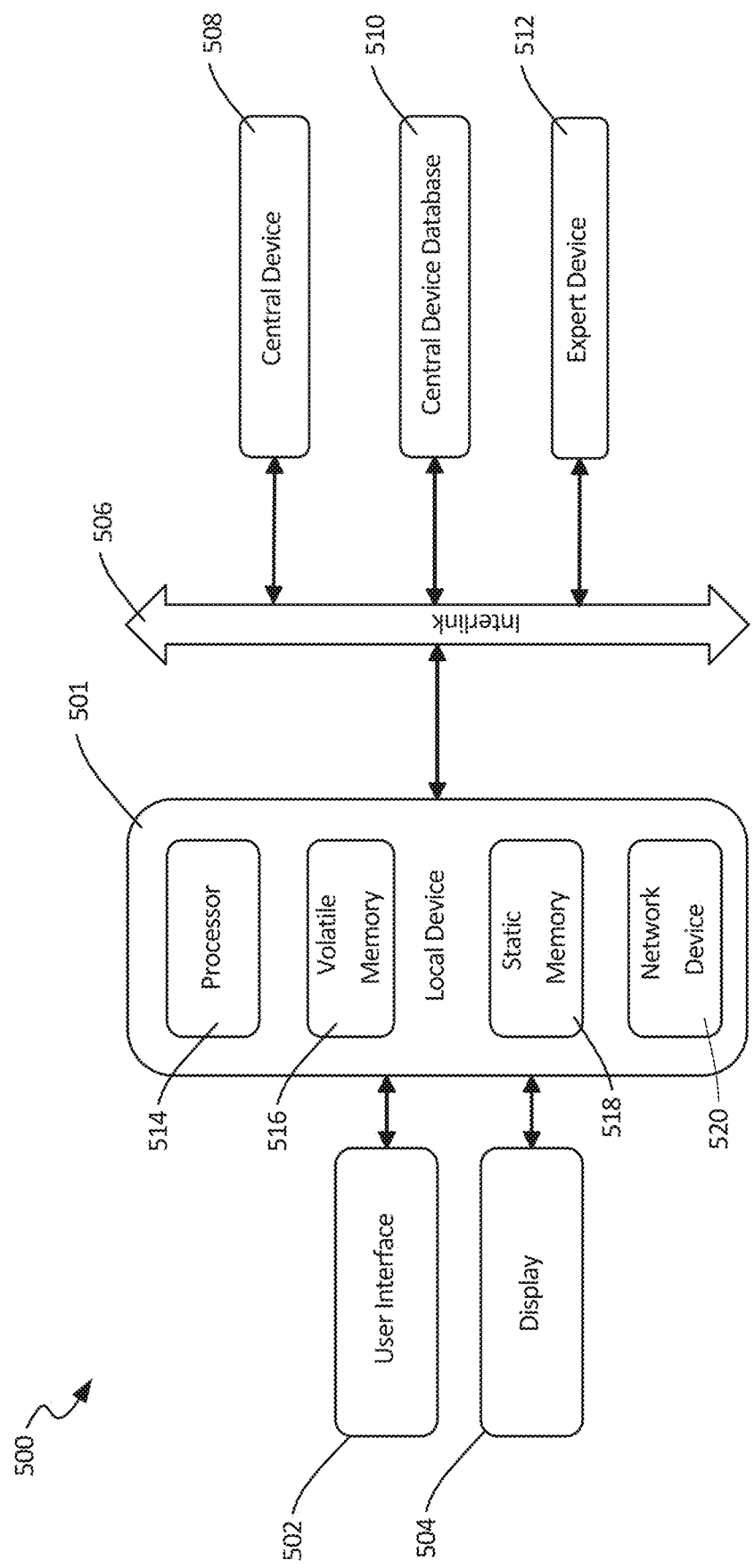
FIG. 5 illustrates schematic showing how a system of the present disclosure can be connected, in accordance with at least one example of this disclosure.

FIG. 5 illustrates schematic showing how system 500 can be connected.

System 500 can include local device 501, user interface 502, display 504, interlink 506, central device 508, central device database 510, and expert device 512. Local device 501 can include processor 514, volatile memory 516, static memory 518, and network device 520.

Local device 501 can be any computing device, such as a handheld computer, for example, a smart phone, a tablet, a laptop, a desktop computer, or any other computing device including information processing and storage capabilities and communication capabilities. Local device 501 can include processor 514, volatile memory 516, and static memory, which can be connected by wire or other electrical conduit within local device 501 and can be configured to receive information, process information, output information, and store information. The information can be temporarily stored on volatile memory 516 and can be relatively permanently stored on static memory 518. In some examples, configurations of these components within local device 501 can be considered machine readable medium.

The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

User interface 502 can be any input and/or output device. For example, user interface can be a monitor, keyboard, and mouse in one example. In other examples, user interface 502 can be a touch screen display. Display 504 can be a display for displaying output from local device 501 and in some examples can receive input and transfer input to local device 501 (for example a touch screen display).

Central device 508 can be a remote device similar in configuration to local device 501, but located remotely from local device 501. Central device 508 can be configured to connect to multiple of local devices 501, in some examples, through interlink 506. Similarly, expert device 512 can be a remote device similar in configuration to local device 501, but can be operated by a user considered to be an expert. In operation of some examples, the expert user can interface with the processes and decisions of the methods discussed herein.

In some examples, user interface and display 504 can be connected to local device 501 through wired connections, in some examples (such as USB, for example), and through wireless connections (such as Bluetooth, for example) in other examples. In some other examples, interlink 506 can be a local area network (LAN), wide area network (WAN), and internet protocol (TCP/IP) connections. Local device 501 can be similarly connected to interlink 506 (either through a wired or wireless connection). In some examples, network device 520 can connect local device 501 to interlink 506. Central device 508, central device database 510, and expert device 512 can be connected to interlink 506 in a similar manner.

In operation of some examples, system 500 can be configured to perform steps of the methods discussed herein and in some examples may perform steps based on a program stored in volatile memory 516 or static memory 518, where results of the analysis are stored in either volatile memory 516 and/or static memory 518 can be displayed on display 504 and/or transmitted to user interface 502, central device 508, central device database 510, and/or expert device 512. For example, system 500 can develop a reverse shoulder arthroplasty plan by receiving an image of a patient shoulder. One of local device 501, central device 508, and expert device 512 can segmented the image to develop a 3D shoulder model.

Then, a device (such as local device 501) can perform virtual surgery on the 3D shoulder model to generate a modified shoulder model. The modified shoulder model can be stored in volatile memory 516 and/or static memory 518. In some examples, the virtual surgery can include resecting and reaming a virtual humerus of the 3D shoulder model, and reaming a virtual glenoid of the 3D shoulder model, which can be displayed for example, on display 504. Thereafter, selection of a humeral implant and selection of a glenoid implant can be received from a user interface, such as user interface 502, in some examples, and can be made by local device in some other examples.

Local device 501, central device 508, or expert device 510 can implant a virtual representation of the humeral implant on the virtual humerus and can implant a virtual representation of the glenoid implant on the virtual glenoid to virtually update the modified shoulder model. The updated modified shoulder model can be stored in volatile memory 516 and/or static memory 518. In some examples, the updated modified shoulder model can be stored in central device 508 or expert device 512. One of local device 501, central device 508, and expert device 510 can then determine a range of motion of the patient shoulder and a reverse shoulder arthroplasty can be finalized based on the range of motion.

Similarly, system 500 can be configured to perform steps of each method discussed herein.

Figure 6:
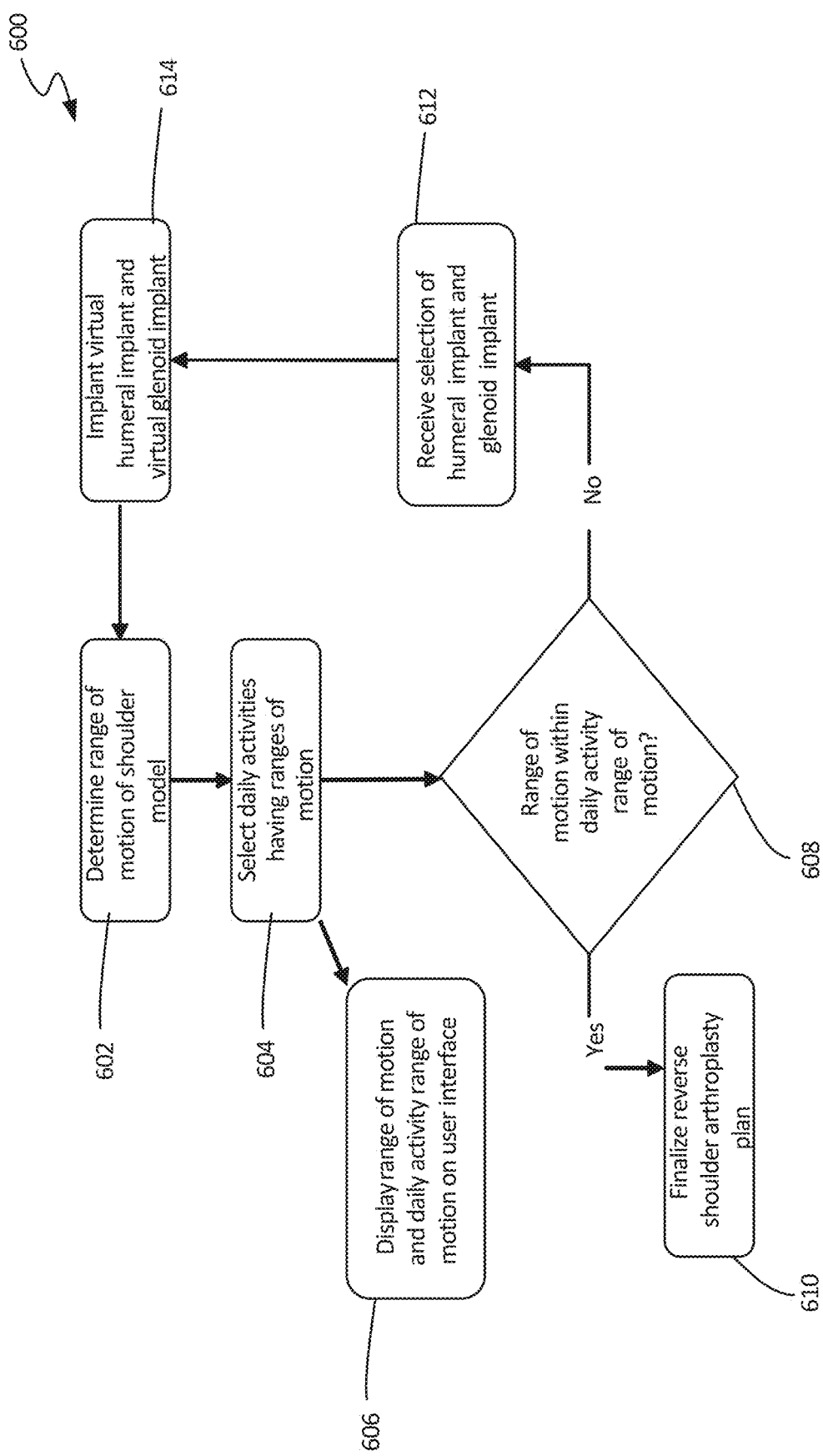
FIG. 6 illustrates a schematic view of another method of using the systems of the present disclosure, in accordance with at least one example of this disclosure.

FIG. 6 illustrates a schematic view of method 600, in accordance with at least one example of this disclosure. At step 602, a range of motion of the shoulder can be determined using the 3D model. As discussed at step 402, the range of motion can be determined using several techniques. Then, at step 604 daily activities can be selected, where each daily activity includes a range of motion. For example, a daily activity such as combing or brushing hair can be selected, which can include a predetermined approximate range of motion. Other daily activities can also be used, such as driving a car, stacking dishes on shelves, and opening a door. In some example, more than one daily activity and its range of motion can be selected. At step 606, the range of motion can be displayed on a user interface, such as a monitor or display. Also, the range of motion of the daily activity or activities can be displayed.

At step 608, it can be determined whether the range of motion derived in step 602 is of an acceptable range of motion. This decision can be determined, in some examples, by comparing the range of motion from step 602 to the range of motion of the daily activity or activities. In some examples, this decision can be made by a device of system 500, for example, and in other examples, this decision can be made by a physician and/or a patient through a user interface and/or monitor. In some examples, the user can then enter the decision into a system at step 608.

When it is determined that the range of motion is within the desired range of motion, a shoulder arthroplasty plan can be finalized at step 610. In some examples, this plan can include a written and/or pictoral plan indicating how the humerus and glenoid should be prepared, as described above. This plan can also indicate daily activities for which the range of motion has been selected, which can be used to guide and track post-operative recovery and therapy.

When it is determined that the range of motion is not within the desired range of motion, a second humeral implant and second glenoid implant can be selected at step 612, which can optionally include adjusting the position and/or orientation of the implant, as described in further detail below with respect to FIGS. 11 and 12. The second humeral implant and the second glenoid implant can be installed on the virtual humerus and virtual glenoid, respectively, at step 614, so that a second range of motion can be determined at step 602 and so that it can be determined if the second range of motion is within the desired range of motion at step 608. Steps 602, 604, 606, 608, 612, and 614 can be repeated as necessary until an acceptable range of motion is determined, at which point step 610 can be performed.

Figure 7:
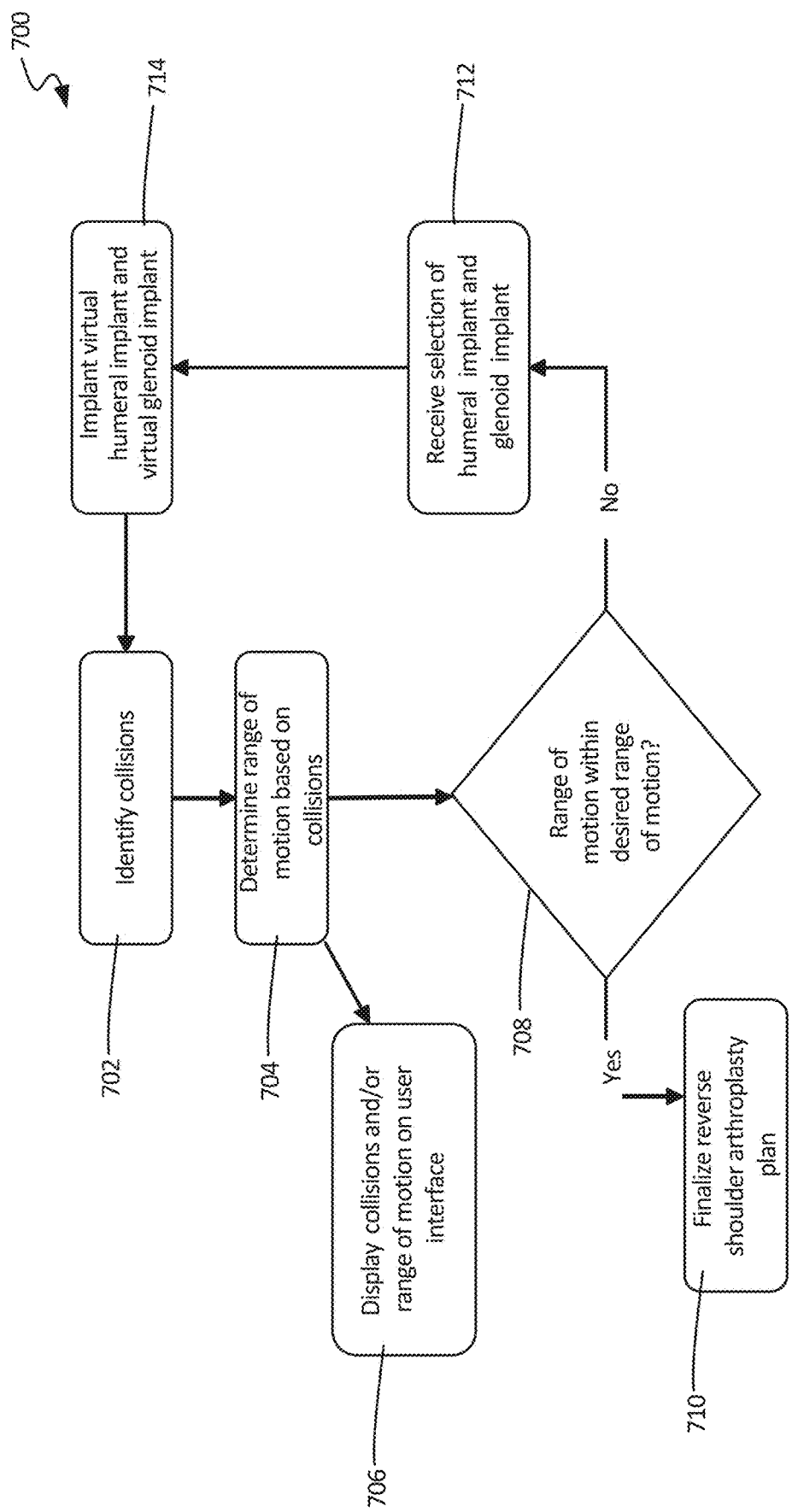
FIG. 7 illustrates a schematic view of another method of using the systems of the present disclosure, in accordance with at least one example of this disclosure.
Figure 8:
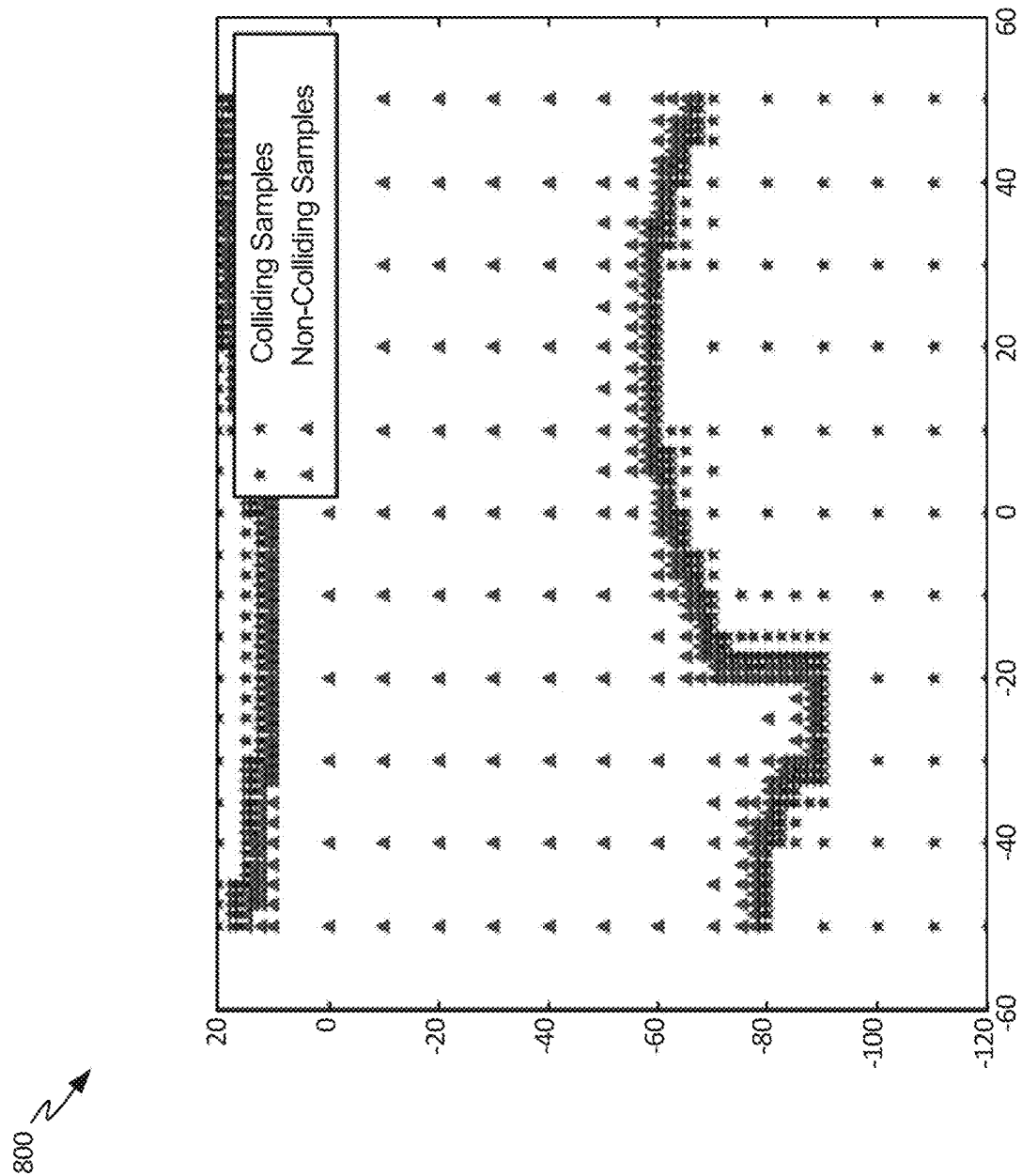
FIG. 8 illustrates a chart that can be displayed on a user interface of the systems of the present disclosure, in accordance with at least one example of this disclosure.

FIG. 7 illustrates a schematic view method 700, in accordance with at least one example of this disclosure. At step 702, the method can begin by identifying collisions. Collisions can be between implant components, between one implant component and a bone, and between bones. For example, a collision can be between a humeral implant and a scapula, as illustrated in FIG. 2 by contact point 120. At step 704, a range of motion of the shoulder can be determined by analyzing the collision (as shown in FIG. 8 below), where the outer limits of the range of motion are non-colliding samples or points of analysis.

At step 706, the range of motion can be displayed on a user interface, such as a monitor or display. Also, the collisions and non-collision points can be displayed on the user interface. At step 708, it can be determined whether the range of motion derived in step 704 is of an acceptable range of motion. In some examples, this decision can be made by a device of system 500, for example, and in other examples, this decision can be made by a physician and/or a patient through a user interface and/or monitor. In some examples, collision locations within the range of motion can be compared to ranges of motion to perform desired daily activities, and if the collision points will not impede daily activities, the range of motion may be deemed acceptable. The user can then enter the decision into a system at step 708. In some examples, the range of motion determined by the collisions can be compared with the range of motion of daily activities (as discussed with reference to FIG. 6).

When it is determined that the range of motion is within the desired range of motion, a shoulder arthroplasty plan can be finalized at step 710. In some examples, this plan can include a written and/or pictoral plan indicating how the humerus and glenoid should be prepared, as described above.

When it is determined that the range of motion is not within the desired range of motion, a second humeral implant and second glenoid implant can be selected at step 712. The second humeral implant and the second glenoid implant can be installed on the virtual humerus and virtual glenoid, respectively, at step 714, so that collisions can again be determined at step 702 and so that it can be determined if the second range of motion is within the desired range of motion at step 708. Steps 702, 704, 706, 708, 712, and 714 can be repeated as necessary until an acceptable range of motion is determined, at which point step 710 can be performed.

FIG. 8 illustrates chart 800 that can be displayed on a user interface of the systems of the present disclosure, in accordance with at least one example of this disclosure.

Chart 800 can include x-axis, y-axis, colliding samples, and non-colliding samples. Both the x-axis and y-axis can be in units of degrees. In some examples, the x-axis can represent flexion and extension and the y-axis can represent adduction and abduction. Colliding samples can be denoted by an asterisk (*) and non-colliding samples can be denoted by a triangle (♦).

Chart 800 can represent collision samples for a single combination of a virtual surgery and implant selection. In examples where either the virtual surgery is changed and/or the implant or implants are changed, another chart can be produced. In each chart, samples can be collected at incremental positions of flexion/extension and adduction/abduction. In some examples, samples can be collected or calculated at increments of 10 degrees. In other examples, samples can be calculated at increments of 1, 2, 3, 4, 5, 6, 8, or 12 degrees.

In some examples, a small increment may be used near a point where a collision has been detected to provide a more precise limit of the range of motion. For example, as shown in FIG. 8, a collision was detected at −50 degrees of extension and −80 degrees of abduction. Accordingly, samples of non-collisions were located at −50 degrees of extension and −79 degrees of abduction and at −50 degrees of extension and −78 degrees of abduction. Similarly, relatively small increments may be used along the x-axis near a limit of a range of motion, such as between −50 and −40 degrees of extension around −79 degrees of abduction, as shown in FIG. 8.

Once a range of motion has been analyzed, a boundary or limit of the range of motion will be determined as all of the points between collision and no collision samples. In the example of FIG. 8, the limits are displayed as a dense collection of non-colliding samples adjacent a collision area or a dense collection of colliding samples, both of which can form lines or curves. A chart displaying limits of the range of motion, such as the chart of FIG. 8, can be displayed using a display or user interface, as described in FIG. 7. Alternatively, the chart can be stored in a matrix or table to be analyzed at a later time.

In either case, the limits of the range of motion can be used to determine whether a range of motion is within a desired range of motion. In some examples, the chart displaying collisions can be overlaid to show daily activity range of motion curve using a different color or indicator, such as a plus sign (+) (not shown in FIG. 8). In these examples, the chart showing the range of motion as determined using collision samples and showing the range of motion of one or more daily activities can be outputted to a display or user interface. A physician and/or a patient can then view the chart to determine whether the range of motion is within a desired range of motion.

Figure 9:
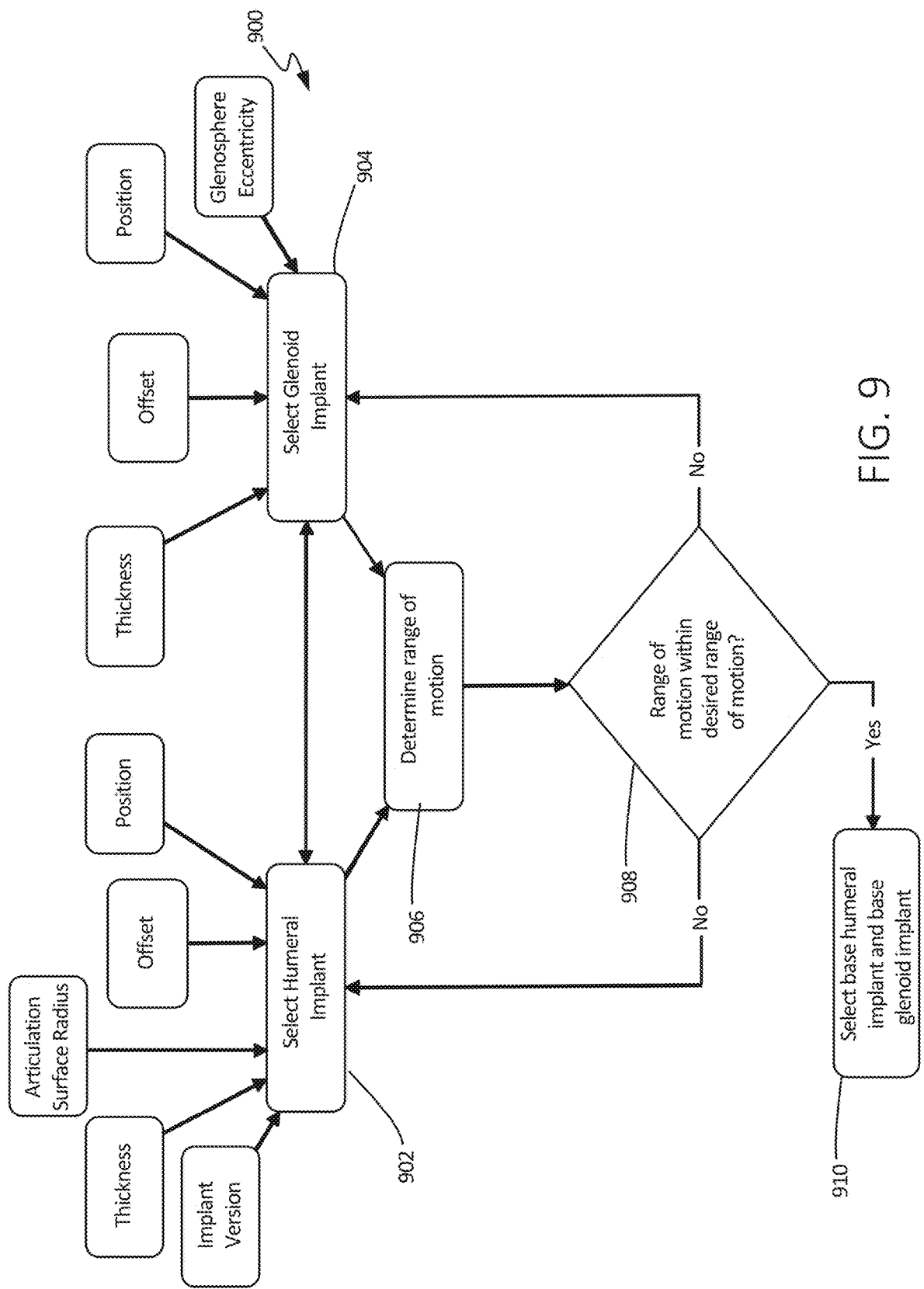
FIG. 9 illustrates a schematic view of another method of using the systems of the present disclosure, in accordance with at least one example of this disclosure.

FIG. 9 illustrates a schematic view of method 900, in accordance with at least one example of this disclosure. Method 900 can begin at step 902, in some examples, where the humeral implant can be selected. The humeral implant can be selected to have a particular thickness, offset, implant version, articulation surface radius, and position, as shown in FIG. 9 and as discussed with reference to FIG. 2 above. Similarly, method 900 can begin at step 904, in some examples, where the glenoid implant can be selected. The glenoid implant can be selected to have a particular thickness, offset, glenosphere eccentricity, and position, as shown in FIG. 9 and as discussed above. Once either step 902 or step 904 has been performed, the other can be performed.

Once both of steps 902 and 904 have been performed, a range of motion can be determined at step 906. In some examples, only one of steps 902 and 904 can be performed, such as during the second iteration of selecting a base component. The range of motion can be determined using one of the several methods discussed above. Then, at step 908, it can be determined whether the range of motion is within a desired range of motion. This determination can be performed by a system, such as system 500, in some examples. When it is determined that the range of motion is within the desired range of motion, a base humeral implant and a base glenoid implant can be determined at step 910.

When it is determined that the range of motion is not within the desired range of motion, a second humeral implant and/or second glenoid implant can be selected at steps 902 and 904. Thereafter, a second range of motion can be determined at step 906 and it can be determined if the second range of motion is within the desired range of motion at step 908. Steps 902, 904, 906, and 908 can be repeated as necessary until an acceptable range of motion is determined, at which point step 910 can be performed.

Figure 10:
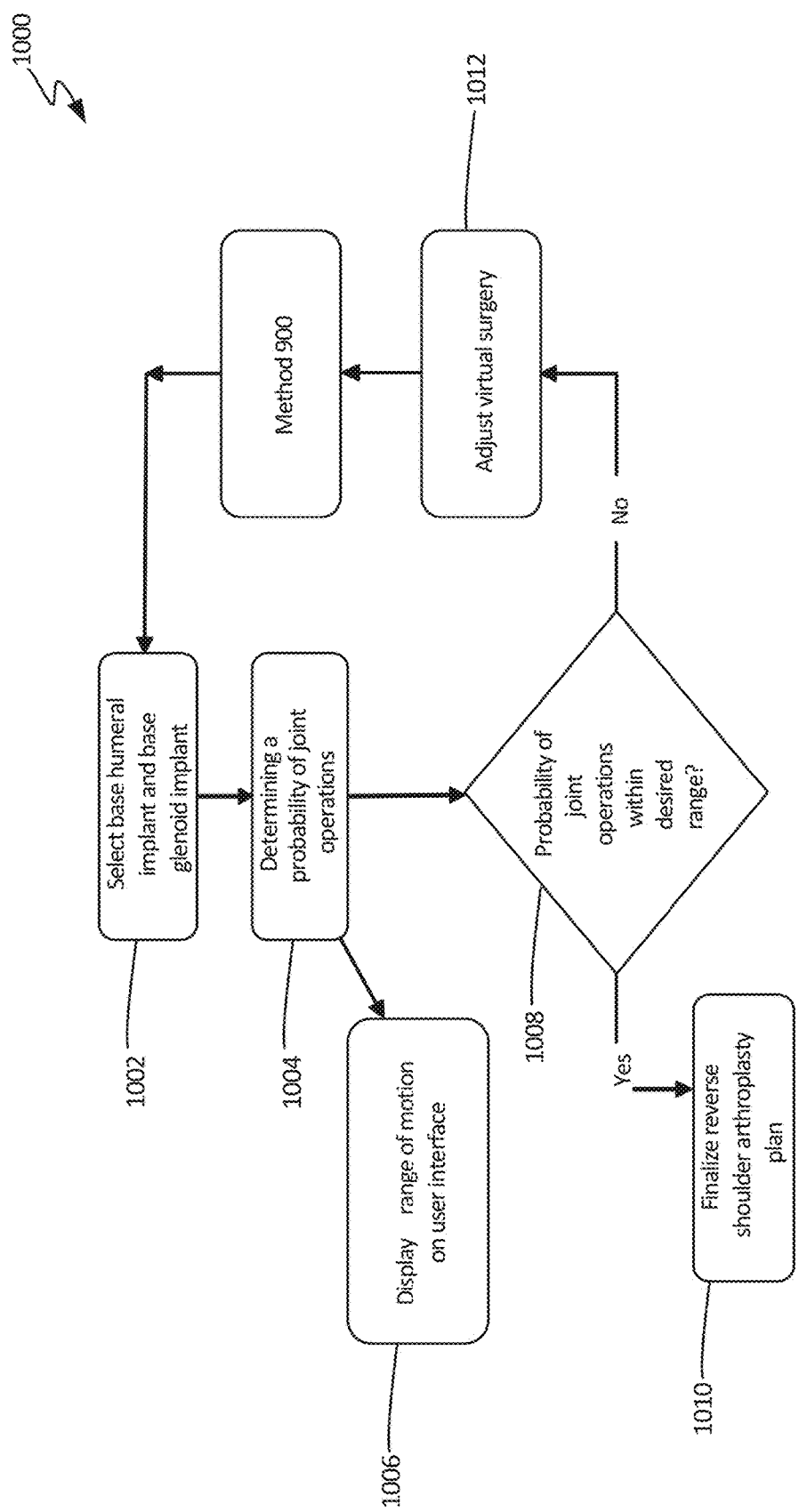
FIG. 10 illustrates a schematic view of another method of using the systems of the present disclosure, in accordance with at least one example of this disclosure.

FIG. 10 illustrates a schematic view of method 1000, in accordance with at least one example of this disclosure. Method 1000 can begin at step 1002, following step 910 of method 900, where a base humeral implant and base glenoid implant can be selected. The base selections can be made as a function of range of motions determined to be within an acceptable range in one of the methods previously discussed. Thereafter, at step 1004, the operations of the joint may be determined to be at a calculated probability. For example, it can be determined, based on the calculated range of motion, a probability of dislocation of the patient's shoulder. In some other examples, a likelihood of joint loosening, joint stability or laxity, or a probability of muscle activation can be determined.

At step 1006, the probable operations of the joint can be displayed on a user interface. At step 1008, it can be determined whether the probable operations of the joint are acceptable. In some examples, this decision can be made by a device of system 500, for example, and in other examples, this decision can be made by a physician and/or a patient through a user interface and/or monitor. The user can then enter the decision into a system at step 1008.

When it is determined that the probable operations of the joint are acceptable, a shoulder arthroplasty plan can be finalized at step 1010. In some examples, this plan can include a written and/or pictoral plan indicating how the humerus and glenoid should be prepared, as described above.

When it is determined that the probable operations of the joint are not acceptable, the virtual surgery can be adjusted at step 1012. This can include modification of resections, connection points of tissues, modifications to reaming, and other aspects of a virtual surgery, discussed in FIG. 3. Further, method 900 can be performed prior to step 1002, where a base humeral implant is reselected as a function of the updated virtual surgery. The second base humeral implant and the second base glenoid implant can be installed on the virtual humerus and virtual glenoid, respectively, so that the probable operations of the joint with the second base implants and the adjusted virtual surgery plan can be determined. Steps 1002, 1004, 1006, 1008, and 1012, can be repeated as necessary until the probable operations of the joint are acceptable, at which point step 1010 can be performed.

Though adjusting the virtual surgery is only discussed with respect to method 1000, the virtual surgery can be adjusted within each of the methods described above. Additionally, analysis of a virtual joint operation to determine probable operations of the joint discussed above can be introduced into any of the methods discussed herein as an additional criteria for judging the virtual surgical plan.

Figure 11:
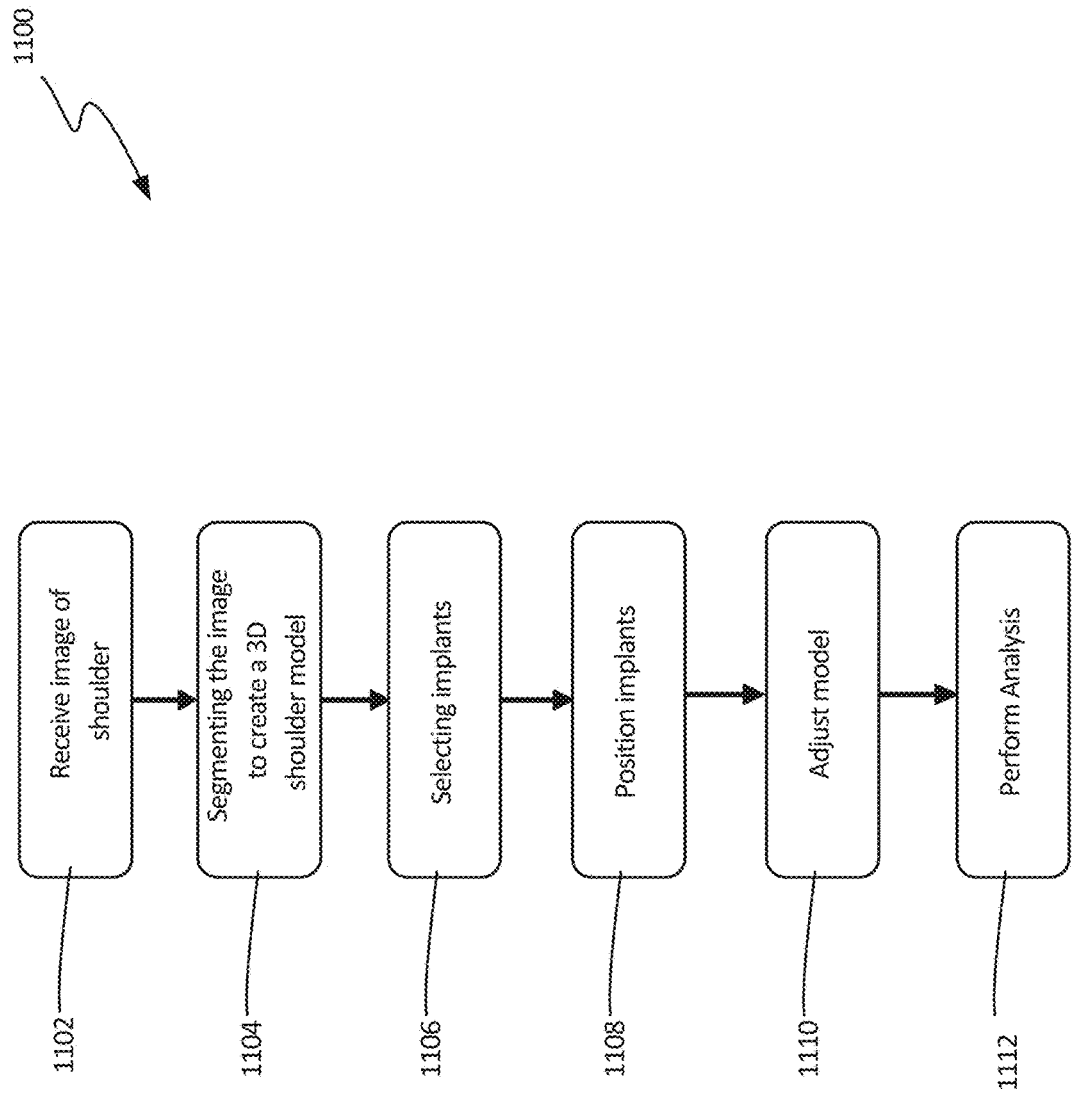
FIG. 11 illustrates a schematic view of another method of using the systems of the present disclosure, in accordance with at least one example of this disclosure.

FIG. 11 illustrates a schematic view of method 1100 using the devices and systems described herein, in accordance with at least one example of this disclosure. In this example, method 1100 can facilitate selection and preliminary analysis implant as first steps towards determining a final shoulder arthroplasty plan. At step 1102, method 1100 can begin with receiving images of a patient's shoulder, such as from a CT or MRI; for example, as described above. Then, at step 1104, the image or images can be segmented to create a 3D virtual model of the patient's shoulder, such as model 100 of FIGS. 1 and 2. Once the model is developed, selection of humeral and glenoid components can be received at step 1106. The selections can be received by the system from another system, received by the system through a user interface, and/or determined by the system through analysis of the 3D virtual model. At step 1108, the virtual humeral implant and virtual glenoid implant, such as humeral and glenoid components 116 and 118 of FIG. 1, can be positioned relative to virtual humerus 102 and virtual glenoid 104, respectively.

In some examples, the computing system, such as system 500, performing or enabling method 1100 can generate a user interface to enable the surgeon to select and position the virtual implants in reference to the virtual bones. In other examples, the initial placement or positioning of the implants can be determined using an algorithm to place the implants relative to the virtual humerus and virtual glenoid. In some examples, the algorithm may include positioning models designed to be a good fit for an average patient. In other examples, the algorithm can include methods tailoring initial placement as a function of the patient's anatomy, such as dimensions of the humerus and glenoid (and therefore scapula). In some examples, automatic placement can be performed using an algorithm defined by literature or developed through testing and research.

In some cases, the model used for analysis, such as finite element analysis (FEA), can be performed using system 500 to adjust the model to match anatomy of the patient at step 1110. For example, soft tissue connection points of the FEA model can be adjusted to match that of the anatomy of the patient. Further, in some examples, humerus and scapula shapes and sizes can be adjusted to match the anatomy of the patient. Once the FEA model has been updated, method 1100 can be continued at step 1112, where analysis can be performed, as described in further detail in the FIGS. below.

Figure 12:
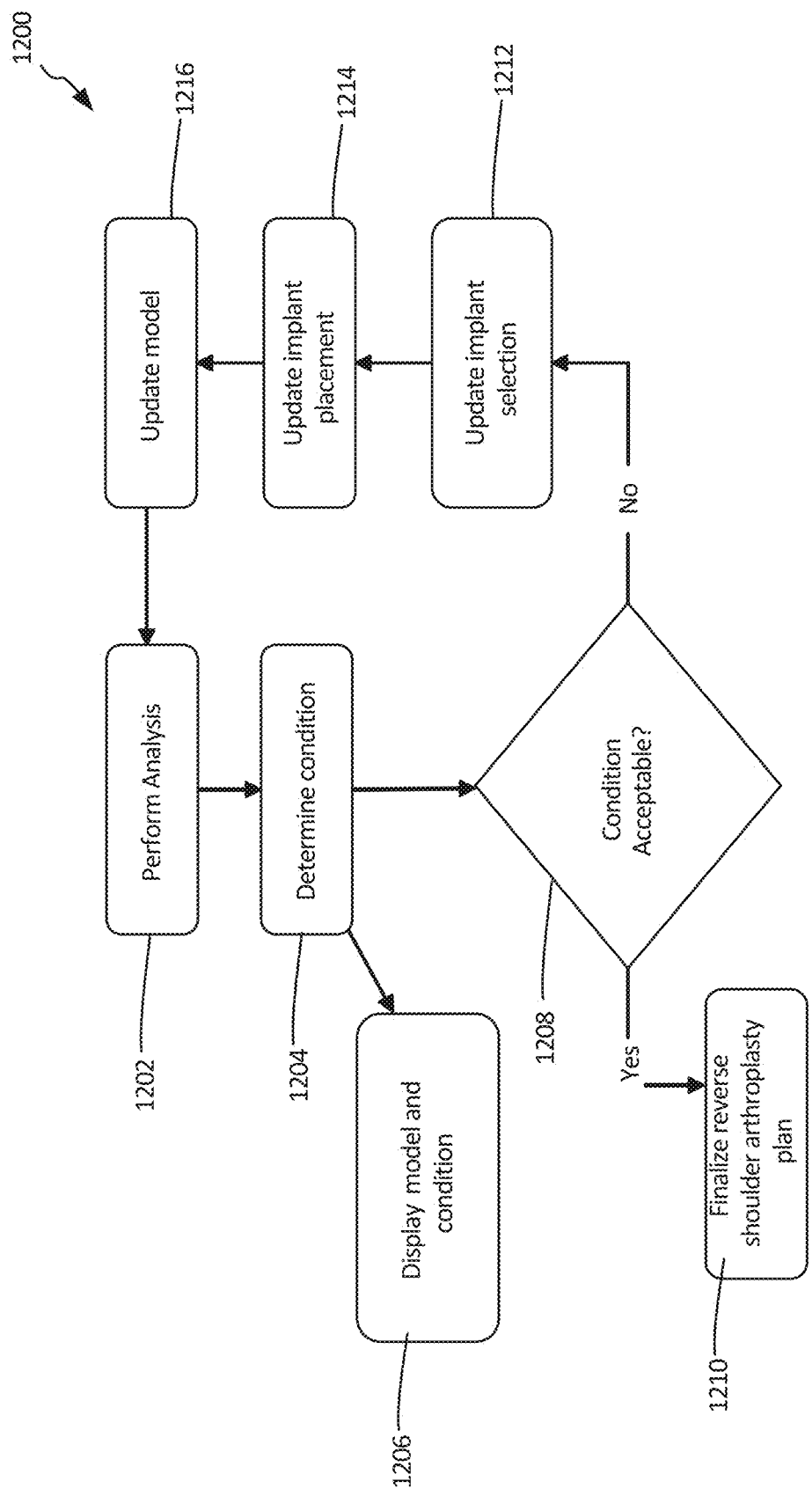
FIG. 12 illustrates a schematic view of another method of using the systems of the present disclosure, in accordance with at least one example of this disclosure.

FIG. 12 illustrates a schematic view of method 1200, which can be continued from step 1112 of method 1100 at step 1202, where analysis can be performed on the model. In some examples, FEA can be performed on the model at step 1202 to determine a condition as an output of the model at step 1204. The condition determined can be a force, stress, strain, range of motion, or other condition of one or more components of the model, such as a bone, soft tissue, or implant, as discussed in detail further below. These conditions can be used to determine whether a model is desirable, that is, if the model when incorporated into an arthroplasty surgical plan is likely to produce acceptable results following the procedure.

At step 1206, the condition can be displayed on user interface 502, such as a monitor or on display 504. In some examples, the condition can be displayed as a graphical display, such as a graphic representation of a human shoulder with an indication of the component and its condition. In other examples, a graph or chart can be used to display the condition. In some other examples, the condition or conditions can be displayed as a list or table of limits.

At step 1208 it can be determined whether the condition is acceptable. For example, it can be determined whether a force on the humerus is within an acceptable range. Other conditions can be determined in some examples, as discussed further below. In some examples, step 1208 can include determination of acceptability of multiple conditions. When it is determined that the condition or conditions is/are acceptable, a shoulder arthroplasty plan can be finalized at step 1210. In some examples, the arthroplasty plan can include a written and/or pictoral plan indicating how the humerus and glenoid should be prepared. This can include, for example, locations and angles of resections and positions and angles of reams. In some examples, the plan can include selection or development of patient specific cut guides or other instruments that can be used inter-operatively to replicate the pre-operative plan during surgery.

When it is determined that condition is not acceptable, the implant selection can be updated at step 1212, which can include selection of a second humeral implant and/or a second glenoid implant. Thereafter, at step 1214, placement of the second humeral implant and/or the second glenoid implant can be determined. The placement can be determined as a function of the analysis of steps 1204 and 1208, in some examples. Once the implant selection and placement have been updated, the model can be updated at step 1216, which can include updating soft tissue connection tension and muscle connections points.

In some examples, the same implants may be used (that is, step 1212 can be skipped) and the position of the humeral implant and/or the glenoid implant can be adjusted. For example, reselection of the implants can be skipped if the condition falls just outside of an acceptable range. In some examples, step 1212 can be skipped, for example, when the analysis of steps 1204 and 1208 indicates that reselection of the implants is not necessary. In lieu of reselection of the implants, the positions of the previously selected implants can be adjusted within the virtual model, which may change how the applicable bones are resected.

After the glenoid implant and humeral implant are virtually repositioned, analysis can be performed again at step 1202. Steps 1202, 1204, 1206, 1208, 1210, 1212, and 1214 can be repeated as necessary until an acceptable condition is determined, at which point step 1210 can be performed.

Figure 13:
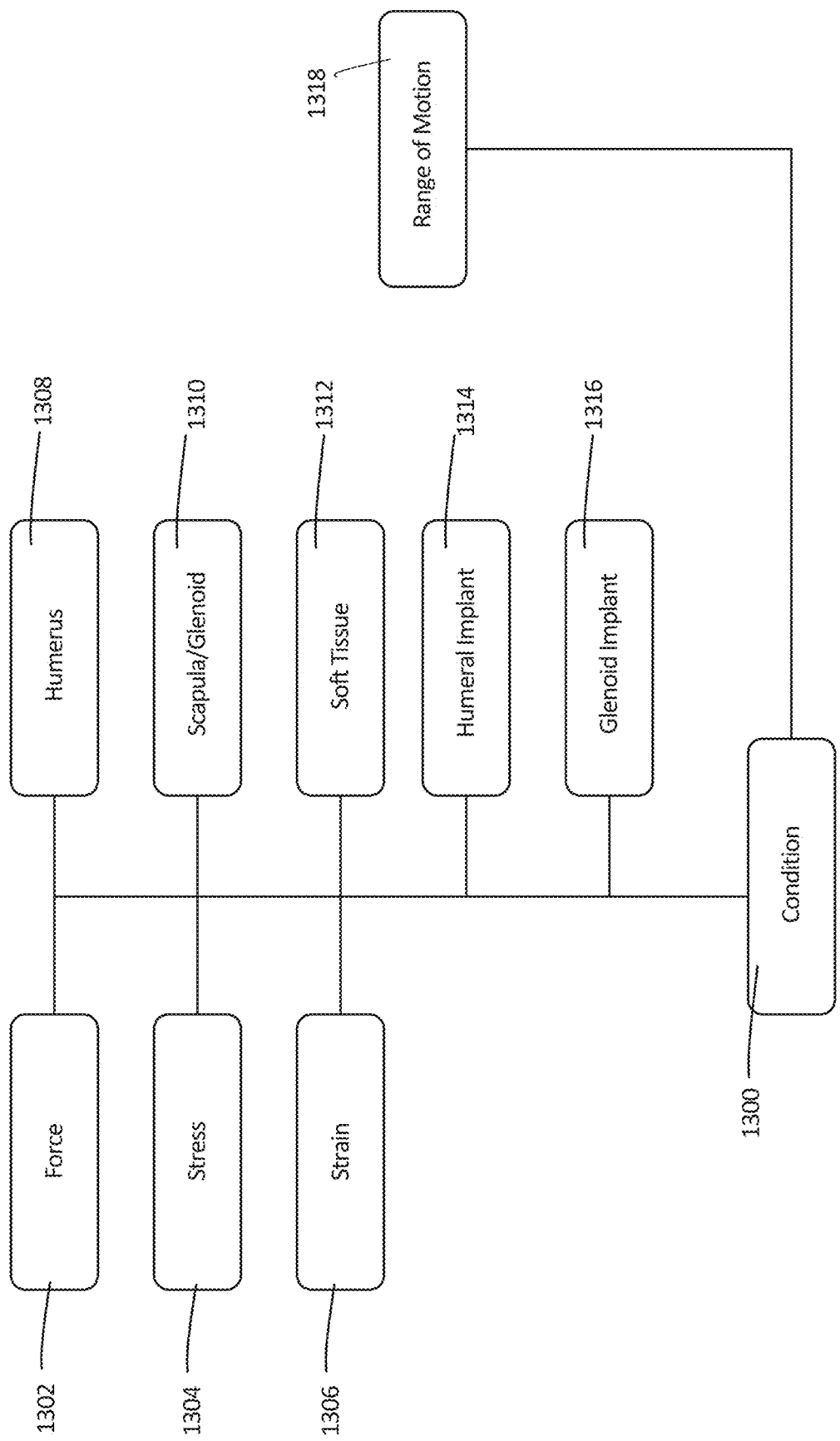
FIG. 13 illustrates a schematic view of inputs for the methods of the present disclosure, in accordance with at least one example of this disclosure.

FIG. 13 illustrates a schematic view of inputs for the methods described herein, in accordance with at least one example of this disclosure. The method shown in FIG. 13 illustrates how condition 1300 can include various inputs that led to calculations or analyses of many components. For example, force 1302, stress 1304, or strain 1306 can be determined for each or all of humerus 1308 (which can be humerus 102), scapula or glenoid 1310 (which can be scapula 104 or glenoid 114), soft tissue 1312 (for example, a deltoid, transverse humeral ligament, etc.), humeral implant 1316 (which can be humeral implant 116), or glenoid implant 1318 (which can be glenoid implant 118). For example, a glenoid implant force can be condition 1300. In other examples, a soft tissue stress can be condition 1300. In some examples, a glenoid implant force and a humeral implant force can be condition 1300.

In some other examples, range of motion 1318 can be condition 1300. For example, a range of motion can be determined via FEA as condition 1300. In some of these examples, the range of motion can be compared to an acceptable range of motion as described with respect to FIGS. 1-10 above. Condition 1300 is not limited to those shown in FIG. 13. For example, additional qualities or conditions of soft tissue 1312 can be used as condition 1300, such as tension of soft tissues. In each example of condition 1300, the condition can be used in the methods described herein to determine the desirability or acceptability of the virtual model.

Figure 14:
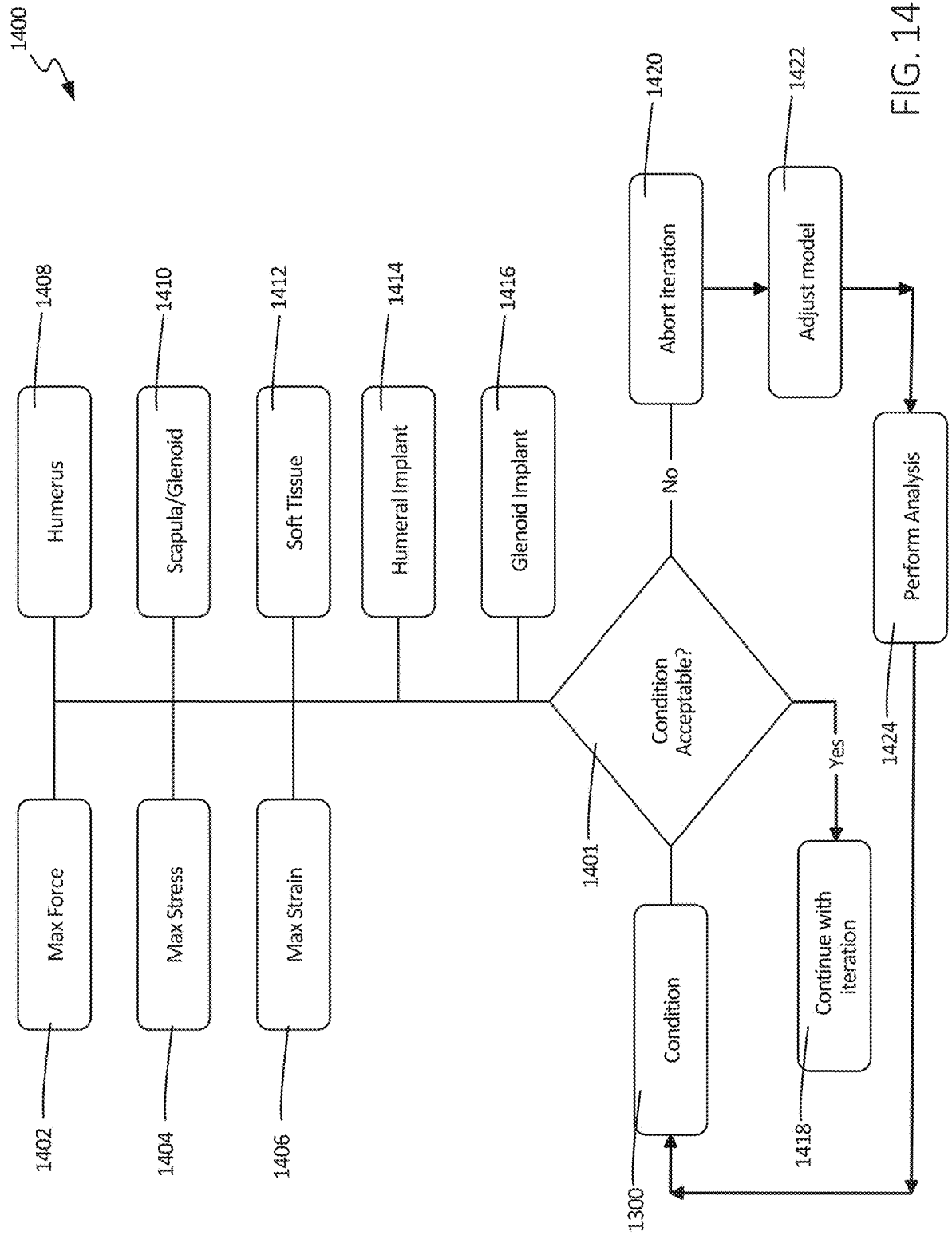
FIG. 14 illustrates a schematic view of another method of using the systems of the present disclosure, in accordance with at least one example of this disclosure.

FIG. 14 illustrates a schematic view of method 1400 using the devices and systems described herein, in accordance with at least one example of this disclosure. FIG. 14 illustrates some examples of how condition 1300 of FIG. 13 can be used.

For example, at step 1401 it can be determined whether condition 1300 is acceptable by comparing condition 1300 to condition limits. Each of max force 1402, max stress 1404, and max strain 1406 can be values for each or all of humerus 1408, glenoid 1410, soft tissue 1412, humeral implant 1414, and glenoid implant 1416. For example, at step 1401 condition 1300 can be compared to max force 1402 of glenoid implant 1416, where condition 1300 can be force 1302 of glenoid implant 1316 of FIG. 13. That is, the max force allowable for a glenoid implant can be compared to the force of the glenoid implant as determined via FEA. In this example, it can be determined whether the force of the glenoid implant derived from FEA is lower than the max glenoid implant force.

The condition limits of elements 1402-1416 are not limited to maximum values. In some examples, minimum values may be used. For example, a minimum force of soft tissue 1412 may be used to determine minimum laxity of the virtual shoulder joint. In some examples, muscle and soft tissue elongation rates can be considered and the modulus of elasticity of the soft tissues can be considered in some other examples. Though in some cases only one condition may be examined, multiple conditions can be used in other examples.

When it is determined at step 1401 that condition 1300 is acceptable, or that condition 1300 is within the range of the limit derived from elements 1402-1416, the iteration of FEA can be continued at step 1418. Thereafter, in some examples, another of condition 1300 can be derived from FEA, in which case step 1401 can be again performed. In other cases, the iteration can be complete, and a plan can be finalized, such as in step 1210 of method 1200. When it is determined at step 1401 that condition 1300 is unacceptable, or that condition 1300 is not within the range of the limit derived from elements 1402-1416, the iteration of FEA can be aborted at step 1420. Thereafter, the model can be adjusted at step 1422 so that a modified model can be analyzed at step 1424 to produce a new condition at condition 1300. In some examples, models can be modified and analyzed until condition 1300 is determined to be acceptable. Thereafter, the same model can produce a different condition, which can thereafter be analyzed at step 1401. This iterative process can continue until all of the conditions of a model are analyzed and/or deemed acceptable.

Figure 15:
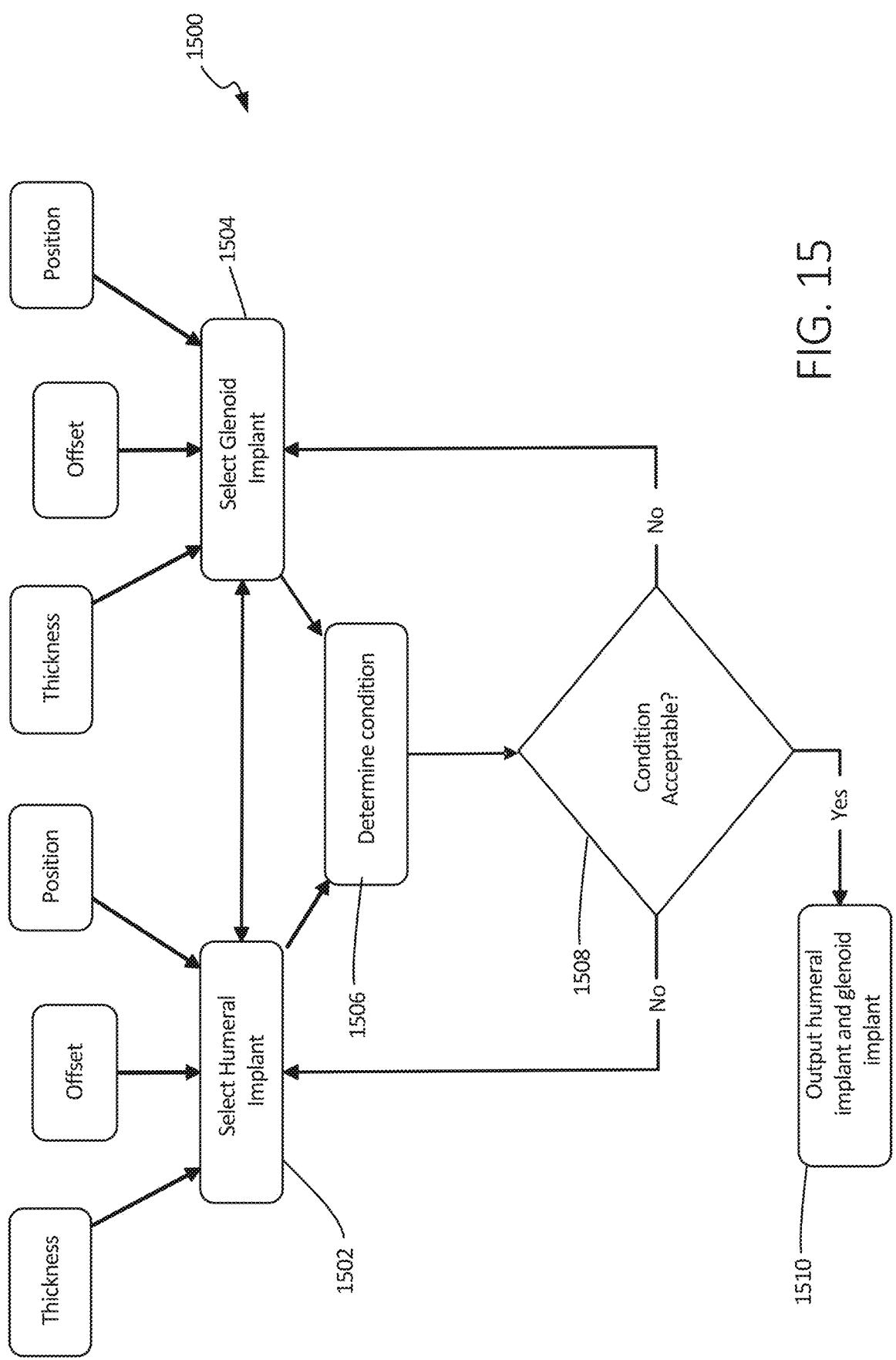
FIG. 15 illustrates a schematic view of another method of using the systems of the present disclosure, in accordance with at least one example of this disclosure.

FIG. 15 illustrates a schematic view of method 1500, in accordance with at least one example of this disclosure. In the example illustrated, method 1500 shows how various attributes or characteristics can be iteratively selected for when choosing humeral and glenoid implants.

Method 1500 can begin at step 1502, in some examples, where the humeral implant can be selected. The humeral implant can be selected to have a particular thickness, offset, and position, as shown in FIG. 15. Similarly, method 1500 can begin at step 1504, in some examples, where the glenoid implant can be selected. The glenoid implant can be selected to have a particular thickness, offset, and position, as shown in FIG. 15. Once either step 1502 or step 1504 has been performed, the other can be performed.

Once both of steps 1502 and 1504 have been performed, a condition can be determined at step 1506. In some examples, only one of steps 1502 and 1504 can be performed, such as during the second iteration of selecting a base component. The condition can be determined using one of the several methods discussed above at step 1508. In some examples, step 1508 can include the entire method of method 1400. When it is determined that the condition is acceptable, a humeral implant and a glenoid implant can be finalized and outputted at step 1510. For example, the output can be received by system 500 and used in another method of the present disclosure, such as method 11, where the entirety of method 15 is used to select implants at step 1108. This can be one method of selecting a set of base implants.

When it is determined that the condition is not acceptable, a second humeral implant and/or second glenoid implant can be selected at steps 1502 and 1504. Thereafter, a second condition can be determined at step 1506 and it can be determined if the second condition is acceptable at step 1508. Steps 1502, 1504, 1506, and 1508 can be repeated as necessary until a condition is acceptable, at which point step 1510 can be performed.

Figure 16:
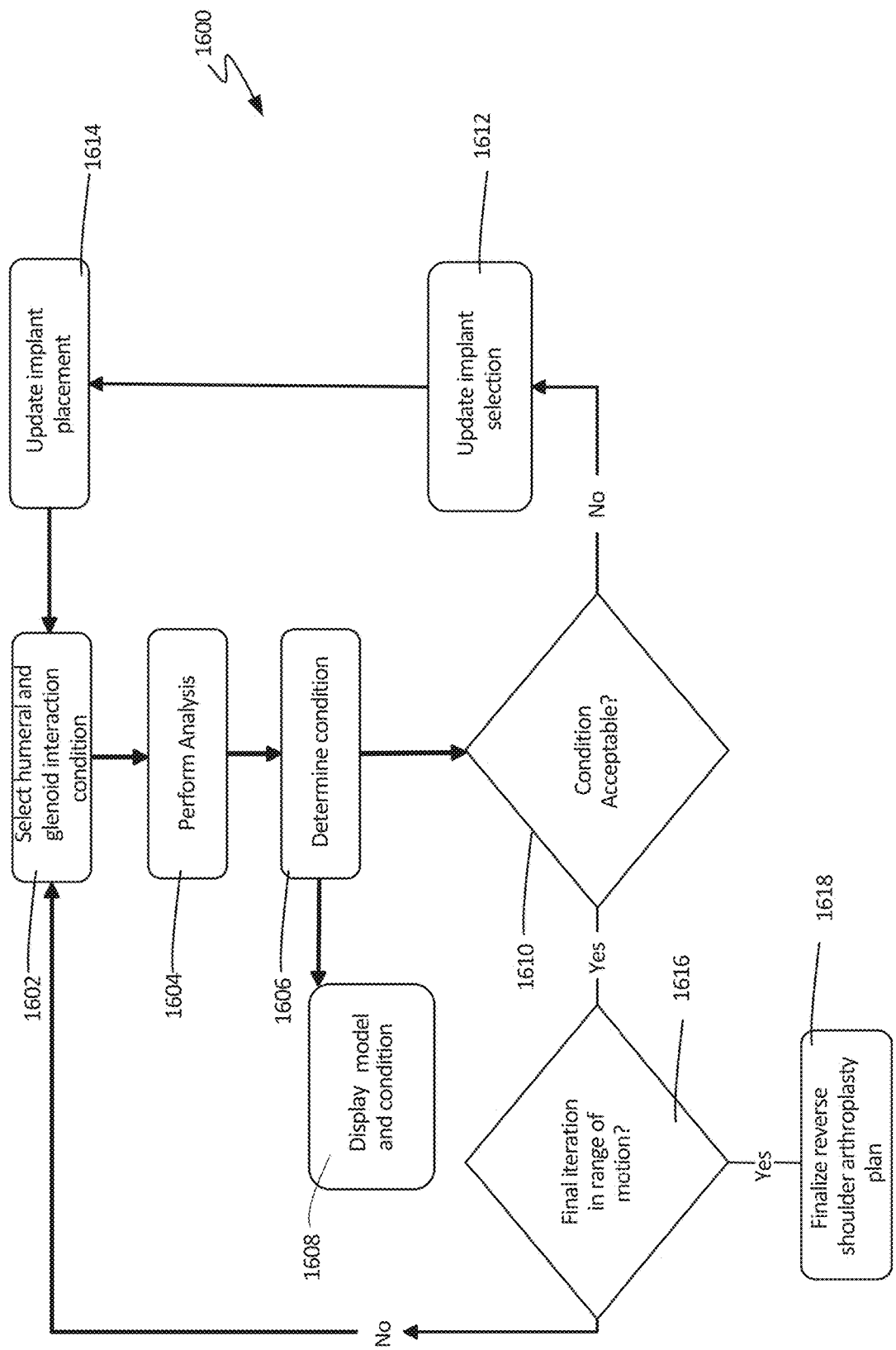
FIG. 16 illustrates a schematic view of another method of using the systems of the present disclosure, in accordance with at least one example of this disclosure.

FIG. 16 illustrates a schematic view of method 1600, which can begin at step 1602, where a first condition is selected, which can be a condition or a position, for example, of humerus 102 relative to scapula 104 or glenoid 114. For example, a first interaction condition may be at a neutral position of the humerus relative to the scapula. Analysis, such as FEA, can then be performed at step 1604 on a model including previously selected implant components (such as in methods 1100 or 1500). The condition can then be outputted from the model at step 1606 and displayed at step 1608.

At step 1610 it can be determined whether the condition is acceptable. For example, it can be determined whether a force on the humerus is within an acceptable range. In some examples, this decision can be made by a system using, for example, a method similar to that of method 1400. In some other examples, or after a system has completed analysis, a user such as a physician, can determine whether the condition is acceptable at step 1600. The system or user can then make adjustments to the model at steps 1612 and 1614, where changes to conditions can be seen by the user at step 1608. In this way, a user can interact with the model to optimize the model and plan based on the experience of the user.

When it is determined that the condition is not acceptable, the implant selection can be updated at step 1612, which can include selection of a second humeral implant and/or a second glenoid implant. Thereafter, at step 1614, placement of the second humeral implant and/or the second glenoid implant can be determined. The placement can be determined as a function of the analysis of steps 1604, 1608, and 1610, in some examples.

When it is determined that the condition is acceptable at step 1610, it can then be determined whether the iteration was the final iteration in the range of motion at step 1616. This can be done, in some examples, by comparing the position of the humerus relative to the glenoid to a list or table of positions requiring analysis. When the range of motion is not the final iteration of the range of motion, a subsequent position can be selected at step 1602. Steps 1602, 1604, 1606, 1608, 1610, 1612, 1614, and 1616 can be performed until a full range of motion has been analyzed and all of the conditions at each position within the range of motion are determined to be acceptable. Once an entire range of motion has been analyzed and all of the conditions are determined to be acceptable, a shoulder arthroplasty plan can be finalized at step 1618.

In some examples, steps 1612 and steps 1614 can be skipped or repeatedly skipped such that conditions of an entire range of motion can be analyzed to determine a set of conditions of the model through the entire range of motion. Thereafter, the set of conditions can be analyzed to determine if each condition is acceptable, allowing for review of all of the conditions of an entire model. In some examples, multiple models can be analyzed and steps 1612 and 1614 can be performed between model selections. In this way, a single model can be selected as a best choice from a set of analyzed models.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A method of pre-operatively developing a shoulder arthroplasty plan, the method comprising:
   receiving an image of a patient shoulder comprising a humerus and a glenoid;
   performing virtual surgery on a three-dimensional (3D) shoulder model, based at least in part on the image, using a system to generate a modified shoulder model including implanting within the 3D shoulder model a virtual representation of a humeral implant on a virtual humerus and a virtual representation of a glenoid implant on a virtual glenoid;
   determining, using the system, a range of motion of the patient shoulder based on finite element analysis of the modified shoulder model including determining an expected interaction between the virtual representation of the humerus implant and the virtual representation of the glenoid implant; and
   selecting, using the system and in response to determining that the range of motion is not within a desired range, at least one of a second humeral implant and a second glenoid implant.

2. The method of claim 1, further comprising:
   aborting an iteration of determining the range of motion of the modified shoulder model when one of a maximum humeral force, a maximum humeral stress, a maximum humeral strain, a glenoid maximum force, a glenoid maximum stress, a glenoid maximum strain, a soft tissue maximum force, and a soft tissue force minimum force is determined.

3. The method of claim 1, wherein determining the range of motion of the modified shoulder model is performed on a static model of the modified shoulder model.

4. The method of claim 3, wherein determining the range of motion of the modified shoulder model is performed on a dynamic model of the modified shoulder throughout a target range of motion of the modified shoulder model.

5. The method of claim 1, further comprising:
   adjusting the modified shoulder model to match anatomy of the patient.

6. The method of claim 5, further comprising:
adjusting soft tissue connection points of the modified shoulder model to match that of corresponding anatomy of the patient.

7. The method of claim 6, further comprising:
adjusting humerus and scapula shapes and sizes of modified shoulder model to match that of corresponding anatomy of the patient.

8. The method of claim 1, wherein:
the virtual representation of the humeral implant includes a humeral implant thickness, offset, and position on the virtual humerus;
the virtual representation of the glenoid implant includes a glenoid implant thickness, offset, and position on the virtual glenoid; and
the selection of one or more of the humeral implant and the glenoid implant is updated by updating a selection of one or more of the thickness, offset, and position of the virtual representation of the humeral implant and virtual representation of the glenoid implant.

9. The method of claim 1, further comprising:
determining, while determining the range of motion, whether one or more of a humeral force, a humeral stress, a humeral strain, a glenoid force, a glenoid stress, a glenoid strain, a humeral implant force, a humeral implant stress, a humeral implant strain, a glenoid implant force, a glenoid implant stress, a glenoid implant strain, a soft tissue force, a soft tissue stress, and a soft tissue strain is within a desired range.

10. The method of claim 9, further comprising:
determining, when the range of motion is not within the desired range, a second range of motion of the patient shoulder based on analysis of the modified shoulder model including determining an expected interaction between the virtual representation of the second humerus implant and the virtual representation of the second glenoid implant.

11. A method of pre-operatively developing a reverse shoulder arthroplasty plan, the method comprising:
receiving an image of a patient shoulder comprising a humerus and a glenoid;
generating, using a system, a three dimensional (3D) shoulder model based, at least in part, on the image;
performing virtual surgery on the 3D shoulder model using the system to implant within the 3D shoulder model, a virtual representation of a humeral implant on a virtual humerus and a virtual representation of a glenoid implant on the virtual glenoid;
determining a range of motion of the patient shoulder based on finite element analysis of the 3D shoulder model including determining an expected interaction between the virtual representation of the humerus implant and the virtual representation of the glenoid implant;
selecting, using the system and in response to determining that the range of motion is not within the desired range, at least one of a second humeral implant and a second glenoid implant; and
determining, when the range of motion is not within a desired range, a second range of motion of the patient shoulder based on finite element analysis of the 3D shoulder model including determining an expected interaction between the virtual representation of the second humerus implant and the second humeral implant and the second glenoid implant.

12. The method of claim 11, further comprising:
displaying on a user interface a graphic representation of the range of motion.

13. The method of claim 12, further comprising:
displaying on the graphic representation of the range of motion and a range of motion required to perform a common daily activity.

14. The method of claim 13, further comprising:
determining whether the 3D shoulder model can perform the common daily activity as a function of the range of motion.

15. The method of claim 14, further comprising:
displaying on the graphic representation of the range of motion and a range of motion required to perform a second common daily activity; and
determining whether the 3D shoulder model can perform the second common daily activity as a function of the range of motion.

16. The method of claim 15, further comprising:
identifying collisions between components of the 3D shoulder model;
developing the range of motion as a function of the identified collisions;
identifying areas of collision as a function of the identified collisions; and
displaying on the graphic representation of the range of motion, the identified areas of collision.

17. The method of claim 11, further comprising:
receiving a thickness adjustment of at least one of the humeral implant and the glenoid implant when the range of motion is not within the desired range;
receiving an offset adjustment of at least one of the humeral implant relative to the humerus and the glenoid implant relative to the glenoid when the range of motion is not within the desired range; and
receiving a position adjustment of at least one of the humeral implant on the virtual humerus and the glenoid implant on the virtual glenoid when the range of motion is not within the desired range.

18. The method of claim 17, further comprising:
selecting a base virtual representation of the humeral implant and a base virtual representation of the glenoid implant as a function of adjusting at least one of thickness, offset, and position of the virtual representation of the humeral implant and the virtual representation of the glenoid implant.

19. The method of claim 18, further comprising:
displaying a graphic representation on a user interface of a range of motion of the 3D shoulder model including the base virtual representation of the humeral implant and the base virtual representation of the glenoid implant; and
adjusting at least one of the base virtual representation of the humeral implant and the base virtual representation of the glenoid implant using the user interface.

20. A method of pre-operatively developing a reverse shoulder arthroplasty plan, the method comprising:
receiving an image of a patient shoulder comprising a humerus and a glenoid;
performing virtual surgery on a three-dimensional (3D) shoulder model using a system generate a modified shoulder model including implanting within the 3D shoulder model a virtual representation of a humeral implant on a virtual humerus and a virtual representation of a glenoid implant on a virtual glenoid;
determining, using the system, an expected interaction between the virtual representation of the humerus implant and the virtual representation of the glenoid implant using finite element analysis; and selecting, using the system, at least one of a second humeral implant and a second glenoid implant based on the expected interaction.

\* \* \* \* \*

UNITED STATES PATENT AND TRADEMARK OFFICE
CERTIFICATE OF CORRECTION

PATENT NO. : 12,150,714 B2
APPLICATION NO. : 17/371287
DATED : November 26, 2024
INVENTOR(S) : Varadarajan et al.

Page 1 of 1

It is certified that error appears in the above-identified patent and that said Letters Patent is hereby corrected as shown below:

In the Claims

In Column 24, Line 61, in Claim 20, after "system", insert --to--

Signed and Sealed this
Eleventh Day of February, 2025

Coke Morgan Stewart
*Acting Director of the United States Patent and Trademark Office*